United States Patent
Gilboa

(10) Patent No.: US 8,696,548 B2
(45) Date of Patent: Apr. 15, 2014

(54) ENDOSCOPE STRUCTURES AND TECHNIQUES FOR NAVIGATING TO A TARGET IN BRANCHED STRUCTURE

(75) Inventor: Pinhas Gilboa, Haifa (IL)

(73) Assignee: Covidien LP, Mansfield, MA (US)

( * ) Notice: Subject to any disclaimer, the term of this patent is extended or adjusted under 35 U.S.C. 154(b) by 158 days.

(21) Appl. No.: 13/157,283

(22) Filed: Jun. 9, 2011

(65) Prior Publication Data

US 2011/0237897 A1 Sep. 29, 2011

Related U.S. Application Data

(60) Division of application No. 11/765,330, filed on Jun. 19, 2007, now Pat. No. 7,998,062, which is a continuation of application No. 10/491,099, filed as application No. PCT/IL2003/000323 on Mar. 29, 2004, now Pat. No. 7,233,820.

(60) Provisional application No. 60/372,804, filed on Apr. 17, 2002, provisional application No. 60/388,758, filed on Jun. 17, 2002, provisional application No. 60/407,951, filed on Sep. 5, 2002.

(51) Int. Cl.
*A61B 1/00* (2006.01)
*A61B 1/01* (2006.01)
*A61B 1/018* (2006.01)

(52) U.S. Cl.
USPC .......... 600/117; 600/104; 600/106; 600/113; 600/114

(58) Field of Classification Search
USPC ......... 600/104, 106, 107, 113, 114, 102, 424, 600/117; 606/1
See application file for complete search history.

(56) References Cited

U.S. PATENT DOCUMENTS

| 1,576,781 A | 3/1926 | Phillips |
|---|---|---|
| 1,735,726 A | 11/1929 | Bornhardt |
| 2,407,845 A | 9/1946 | Nemeyer |
| 2,650,588 A | 9/1953 | Drew |
| 2,697,433 A | 12/1954 | Sehnder |

(Continued)

FOREIGN PATENT DOCUMENTS

| CA | 964149 | 3/1975 |
|---|---|---|
| DE | 30 42 343 A1 | 6/1982 |

(Continued)

OTHER PUBLICATIONS

United States Patent and Trademark Office, Notice of Allowance mailed Apr. 6, 2011 in U.S. Appl. No. 11/765,330, 9 pages.

(Continued)

*Primary Examiner* — John P Leubecker

(57) ABSTRACT

Systems and methods employing a small gauge steerable catheter (30) including a locatable guide (32) with a sheath (40), particularly as an enhancement to a bronchoscope (14). A typical procedure is as follows. The location of a target in a reference coordinate system is detected or imported. The catheter (30) is navigated to the target which tracking the distal tip (34) of the guide (32) in the reference coordinate system. Insertion of the catheter is typically via a working channel of a convention bronchoscope. Once the tip of the catheter is positioned at the target, the guide (32) is withdrawn, leaving the sheath (40) secured in place. The sheath (40) is then used as a guide channel to direct a medical tool to target.

10 Claims, 18 Drawing Sheets

(56) References Cited

U.S. PATENT DOCUMENTS

| | | | |
|---|---|---|---|
| 3,016,899 | A | 1/1962 | Stenvall |
| 3,017,887 | A | 1/1962 | Heyer |
| 3,061,936 | A | 11/1962 | Dobbeleer |
| 3,073,310 | A | 1/1963 | Mocarski |
| 3,109,588 | A | 11/1963 | Polhemus et al. |
| 3,294,083 | A | 12/1966 | Alderson |
| 3,367,326 | A | 2/1968 | Frazier |
| 3,439,256 | A | 4/1969 | Kahne et al. |
| 3,577,160 | A | 5/1971 | White |
| 3,614,950 | A | 10/1971 | Rabey |
| 3,644,825 | A | 2/1972 | Davis, Jr. et al. |
| 3,674,014 | A | 7/1972 | Tillander |
| 3,702,935 | A | 11/1972 | Carey et al. |
| 3,704,707 | A | 12/1972 | Halloran |
| 3,821,469 | A | 6/1974 | Whetstone et al. |
| 3,822,697 | A * | 7/1974 | Komiya ........................ 600/114 |
| 3,868,565 | A | 2/1975 | Kuipers |
| 3,941,127 | A | 3/1976 | Froning |
| 3,983,474 | A | 9/1976 | Kuipers |
| 4,017,858 | A | 4/1977 | Kuipers |
| 4,037,592 | A | 7/1977 | Kronner |
| 4,052,620 | A | 10/1977 | Brunnett |
| 4,054,881 | A | 10/1977 | Raab |
| 4,117,337 | A | 9/1978 | Staats |
| 4,173,228 | A | 11/1979 | Van Steenwyk et al. |
| 4,182,312 | A | 1/1980 | Mushabac |
| 4,202,349 | A | 5/1980 | Jones |
| 4,228,799 | A | 10/1980 | Anichkov et al. |
| 4,256,112 | A | 3/1981 | Kopf et al. |
| 4,262,306 | A | 4/1981 | Renner |
| 4,287,809 | A | 9/1981 | Egli et al. |
| 4,298,874 | A | 11/1981 | Kuipers |
| 4,314,251 | A | 2/1982 | Raab |
| 4,317,078 | A | 2/1982 | Weed et al. |
| 4,319,136 | A | 3/1982 | Jinkins |
| 4,328,548 | A | 5/1982 | Crow et al. |
| 4,328,813 | A | 5/1982 | Ray |
| 4,339,953 | A | 7/1982 | Iwasaki |
| 4,341,220 | A | 7/1982 | Perry |
| 4,346,384 | A | 8/1982 | Raab |
| 4,358,856 | A | 11/1982 | Stivender et al. |
| 4,368,536 | A | 1/1983 | Pfeiler |
| 4,396,885 | A | 8/1983 | Constant |
| 4,396,945 | A | 8/1983 | DiMatteo et al. |
| 4,403,321 | A | 9/1983 | Kruger |
| 4,418,422 | A | 11/1983 | Richter et al. |
| 4,419,012 | A | 12/1983 | Stephenson et al. |
| 4,422,041 | A | 12/1983 | Lienau |
| 4,431,005 | A | 2/1984 | McCormick |
| 4,447,224 | A | 5/1984 | Decant, Jr. et al. |
| 4,485,815 | A | 12/1984 | Amplatz |
| 4,506,676 | A | 3/1985 | Duska |
| 4,543,959 | A | 10/1985 | Sepponen |
| 4,548,208 | A | 10/1985 | Niemi |
| 4,571,834 | A | 2/1986 | Fraser et al. |
| 4,572,198 | A | 2/1986 | Codrington |
| 4,583,538 | A | 4/1986 | Onik et al. |
| 4,584,577 | A | 4/1986 | Temple |
| 4,608,977 | A | 9/1986 | Brown |
| 4,613,866 | A | 9/1986 | Blood |
| 4,617,925 | A | 10/1986 | Laitinen |
| 4,618,978 | A | 10/1986 | Cosman |
| 4,621,628 | A | 11/1986 | Budermann |
| 4,625,718 | A | 12/1986 | Olerud et al. |
| 4,638,798 | A | 1/1987 | Shelden et al. |
| 4,642,786 | A | 2/1987 | Hansen |
| 4,645,343 | A | 2/1987 | Stockdale et al. |
| 4,649,504 | A | 3/1987 | Krouglicof et al. |
| 4,651,732 | A | 3/1987 | Frederick |
| 4,653,509 | A | 3/1987 | Oloff et al. |
| 4,659,971 | A | 4/1987 | Suzuki et al. |
| 4,660,970 | A | 4/1987 | Ferrano |
| 4,673,352 | A | 6/1987 | Hansen |
| 4,688,037 | A | 8/1987 | Krieg |
| 4,696,544 | A | 9/1987 | Costella |
| 4,701,049 | A | 10/1987 | Beckmann et al. |
| 4,705,395 | A | 11/1987 | Hageniers |
| 4,705,401 | A | 11/1987 | Addleman et al. |
| 4,706,665 | A | 11/1987 | Gouda |
| 4,709,156 | A | 11/1987 | Murphy et al. |
| 4,710,708 | A | 12/1987 | Rorden et al. |
| 4,719,419 | A | 1/1988 | Dawley |
| 4,722,056 | A | 1/1988 | Roberts et al. |
| 4,722,336 | A | 2/1988 | Kim et al. |
| 4,723,544 | A | 2/1988 | Moore et al. |
| 4,726,355 | A | 2/1988 | Okada |
| 4,727,565 | A | 2/1988 | Ericson |
| RE32,619 | E | 3/1988 | Damadian |
| 4,733,969 | A | 3/1988 | Case et al. |
| 4,737,032 | A | 4/1988 | Addleman et al. |
| 4,737,794 | A | 4/1988 | Jones |
| 4,737,921 | A | 4/1988 | Goldwasser et al. |
| 4,742,356 | A | 5/1988 | Kuipers |
| 4,742,815 | A | 5/1988 | Ninan et al. |
| 4,743,770 | A | 5/1988 | Lee |
| 4,743,771 | A | 5/1988 | Sacks et al. |
| 4,745,290 | A | 5/1988 | Frankel et al. |
| 4,750,487 | A | 6/1988 | Zanetti |
| 4,753,528 | A | 6/1988 | Hines et al. |
| 4,761,072 | A | 8/1988 | Pryor |
| 4,764,016 | A | 8/1988 | Johansson |
| 4,771,787 | A | 9/1988 | Wurster et al. |
| 4,779,212 | A | 10/1988 | Levy |
| 4,782,239 | A | 11/1988 | Hirose et al. |
| 4,784,117 | A | 11/1988 | Miyazaki |
| 4,788,481 | A | 11/1988 | Niwa |
| 4,791,934 | A | 12/1988 | Brunnett |
| 4,793,355 | A | 12/1988 | Crum et al. |
| 4,794,262 | A | 12/1988 | Sato et al. |
| 4,797,907 | A | 1/1989 | Anderton |
| 4,803,976 | A | 2/1989 | Frigg et al. |
| 4,804,261 | A | 2/1989 | Kirschen |
| 4,805,615 | A | 2/1989 | Carol |
| 4,809,694 | A | 3/1989 | Ferrara |
| 4,821,200 | A | 4/1989 | Oberg |
| 4,821,206 | A | 4/1989 | Arora |
| 4,821,731 | A | 4/1989 | Martinelli et al. |
| 4,822,163 | A | 4/1989 | Schmidt |
| 4,825,091 | A | 4/1989 | Breyer et al. |
| 4,829,373 | A | 5/1989 | Leberl et al. |
| 4,836,778 | A | 6/1989 | Baumrind et al. |
| 4,838,265 | A | 6/1989 | Cosman et al. |
| 4,841,967 | A | 6/1989 | Chang et al. |
| 4,845,771 | A | 7/1989 | Wislocki et al. |
| 4,849,692 | A | 7/1989 | Blood |
| 4,860,331 | A | 8/1989 | Williams et al. |
| 4,862,893 | A | 9/1989 | Martinelli |
| 4,869,247 | A | 9/1989 | Howard, III et al. |
| 4,875,165 | A | 10/1989 | Fencil et al. |
| 4,875,478 | A | 10/1989 | Chen |
| 4,884,566 | A | 12/1989 | Mountz et al. |
| 4,889,526 | A | 12/1989 | Rauscher et al. |
| 4,896,673 | A | 1/1990 | Rose et al. |
| 4,905,698 | A | 3/1990 | Strohl et al. |
| 4,923,459 | A | 5/1990 | Nambu |
| 4,931,056 | A | 6/1990 | Ghajar et al. |
| 4,945,305 | A | 7/1990 | Blood |
| 4,945,914 | A | 8/1990 | Allen |
| 4,951,653 | A | 8/1990 | Fry et al. |
| 4,955,891 | A | 9/1990 | Carol |
| 4,961,422 | A | 10/1990 | Marchosky et al. |
| 4,977,655 | A | 12/1990 | Martinelli |
| 4,989,608 | A | 2/1991 | Ratner |
| 4,991,579 | A | 2/1991 | Allen |
| 5,002,058 | A | 3/1991 | Martinelli |
| 5,005,592 | A | 4/1991 | Cartmell |
| 5,013,317 | A | 5/1991 | Cole et al. |
| 5,016,639 | A | 5/1991 | Allen |
| 5,017,139 | A | 5/1991 | Mushabac |
| 5,027,818 | A | 7/1991 | Bova et al. |
| 5,030,196 | A | 7/1991 | Inoue |
| 5,030,222 | A | 7/1991 | Calandruccio et al. |
| 5,031,203 | A | 7/1991 | Trecha |
| 5,042,486 | A | 8/1991 | Pfeiler et al. |

(56) References Cited

U.S. PATENT DOCUMENTS

| | | |
|---|---|---|
| 5,047,036 A | 9/1991 | Koutrouvelis |
| 5,050,608 A | 9/1991 | Watanabe et al. |
| 5,054,492 A | 10/1991 | Scribner et al. |
| 5,057,095 A | 10/1991 | Fabian |
| 5,059,789 A | 10/1991 | Salcudean |
| 5,078,140 A | 1/1992 | Kwoh |
| 5,079,699 A | 1/1992 | Tuy et al. |
| 5,086,401 A | 2/1992 | Glassman et al. |
| 5,094,241 A | 3/1992 | Allen |
| 5,097,839 A | 3/1992 | Allen |
| 5,098,426 A | 3/1992 | Sklar et al. |
| 5,099,845 A | 3/1992 | Besz et al. |
| 5,099,846 A | 3/1992 | Hardy |
| 5,104,393 A | 4/1992 | Isner et al. |
| 5,105,829 A | 4/1992 | Fabian et al. |
| 5,107,839 A | 4/1992 | Houdek et al. |
| 5,107,843 A | 4/1992 | Aarnio et al. |
| 5,107,862 A | 4/1992 | Fabian et al. |
| 5,109,194 A | 4/1992 | Cantaloube |
| 5,119,817 A | 6/1992 | Allen |
| 5,127,408 A | 7/1992 | Parsons et al. |
| 5,142,930 A | 9/1992 | Allen et al. |
| 5,143,076 A | 9/1992 | Hardy et al. |
| 5,152,277 A | 10/1992 | Honda et al. |
| 5,152,288 A | 10/1992 | Hoenig et al. |
| 5,160,337 A | 11/1992 | Cosman |
| 5,161,536 A | 11/1992 | Vilkomerson et al. |
| 5,178,130 A | 1/1993 | Kaiya |
| 5,178,164 A | 1/1993 | Allen |
| 5,178,621 A | 1/1993 | Cook et al. |
| 5,186,174 A | 2/1993 | Schlondorff et al. |
| 5,187,475 A | 2/1993 | Wagener et al. |
| 5,188,126 A | 2/1993 | Fabian et al. |
| 5,190,059 A | 3/1993 | Fabian et al. |
| 5,193,106 A | 3/1993 | DeSena |
| 5,196,928 A | 3/1993 | Karasawa et al. |
| 5,197,476 A | 3/1993 | Nowacki et al. |
| 5,197,965 A | 3/1993 | Cherry et al. |
| 5,198,768 A | 3/1993 | Keren |
| 5,198,877 A | 3/1993 | Schulz |
| 5,207,688 A | 5/1993 | Carol |
| 5,211,164 A | 5/1993 | Allen |
| 5,211,165 A | 5/1993 | Dumoulin et al. |
| 5,211,176 A | 5/1993 | Ishiguro et al. |
| 5,212,720 A | 5/1993 | Landi et al. |
| 5,214,615 A | 5/1993 | Bauer |
| 5,219,351 A | 6/1993 | Teubner et al. |
| 5,222,499 A | 6/1993 | Allen et al. |
| 5,224,049 A | 6/1993 | Mushabac |
| 5,228,442 A | 7/1993 | Imran |
| 5,230,338 A | 7/1993 | Allen et al. |
| 5,230,623 A | 7/1993 | Guthrie et al. |
| 5,233,990 A | 8/1993 | Barnea |
| 5,237,996 A | 8/1993 | Waldman et al. |
| 5,249,581 A | 10/1993 | Horbal et al. |
| 5,251,127 A | 10/1993 | Raab |
| 5,251,635 A | 10/1993 | Dumoulin et al. |
| 5,253,647 A | 10/1993 | Takahashi et al. |
| 5,255,680 A | 10/1993 | Darrow et al. |
| 5,257,636 A | 11/1993 | White |
| 5,257,998 A | 11/1993 | Ota et al. |
| 5,261,404 A | 11/1993 | Mick et al. |
| 5,265,610 A | 11/1993 | Darrow et al. |
| 5,265,611 A | 11/1993 | Hoenig et al. |
| 5,269,759 A | 12/1993 | Hernandez et al. |
| 5,271,400 A | 12/1993 | Dumoulin et al. |
| 5,273,025 A | 12/1993 | Sakiyama et al. |
| 5,274,551 A | 12/1993 | Corby, Jr. |
| 5,279,309 A | 1/1994 | Taylor et al. |
| 5,285,787 A | 2/1994 | Machida |
| 5,291,199 A | 3/1994 | Overman et al. |
| 5,291,889 A | 3/1994 | Kenet et al. |
| 5,295,483 A | 3/1994 | Nowacki et al. |
| 5,297,549 A | 3/1994 | Beatty et al. |
| 5,299,253 A | 3/1994 | Wessels |
| 5,299,254 A | 3/1994 | Dancer et al. |
| 5,299,288 A | 3/1994 | Glassman et al. |
| 5,300,080 A | 4/1994 | Clayman et al. |
| 5,301,061 A | 4/1994 | Nakada et al. |
| 5,305,091 A | 4/1994 | Gelbart et al. |
| 5,305,203 A | 4/1994 | Raab |
| 5,306,271 A | 4/1994 | Zinreich et al. |
| 5,307,072 A | 4/1994 | Jones, Jr. |
| 5,309,913 A | 5/1994 | Kormos et al. |
| 5,315,630 A | 5/1994 | Sturm et al. |
| 5,316,024 A | 5/1994 | Hirschi et al. |
| 5,318,025 A | 6/1994 | Dumoulin et al. |
| 5,320,111 A | 6/1994 | Livingston |
| 5,325,728 A | 7/1994 | Zimmerman et al. |
| 5,325,873 A | 7/1994 | Hirschi et al. |
| 5,329,944 A | 7/1994 | Fabian et al. |
| 5,330,485 A | 7/1994 | Clayman et al. |
| 5,333,168 A | 7/1994 | Fernandes et al. |
| 5,353,795 A | 10/1994 | Souza et al. |
| 5,353,800 A | 10/1994 | Pohndorf et al. |
| 5,353,807 A | 10/1994 | DeMarco |
| 5,359,417 A | 10/1994 | Muller et al. |
| 5,368,030 A | 11/1994 | Zinreich et al. |
| 5,371,778 A | 12/1994 | Yanof et al. |
| 5,375,596 A | 12/1994 | Twiss et al. |
| 5,377,678 A | 1/1995 | Dumoulin et al. |
| 5,383,454 A | 1/1995 | Bucholz |
| 5,385,146 A | 1/1995 | Goldreyer |
| 5,385,148 A | 1/1995 | Lesh et al. |
| 5,386,828 A | 2/1995 | Owens et al. |
| 5,389,101 A | 2/1995 | Heilbrun et al. |
| 5,391,199 A | 2/1995 | Ben-Haim |
| 5,394,457 A | 2/1995 | Leibinger et al. |
| 5,394,875 A | 3/1995 | Lewis et al. |
| 5,397,329 A | 3/1995 | Allen |
| 5,398,684 A | 3/1995 | Hardy |
| 5,399,146 A | 3/1995 | Nowacki et al. |
| 5,400,384 A | 3/1995 | Fernandes et al. |
| 5,402,801 A | 4/1995 | Taylor |
| 5,408,409 A | 4/1995 | Glassman et al. |
| 5,413,573 A | 5/1995 | Koivukangas |
| 5,417,210 A | 5/1995 | Funda et al. |
| 5,419,325 A | 5/1995 | Dumoulin et al. |
| 5,423,334 A | 6/1995 | Jordan |
| 5,425,367 A | 6/1995 | Shapiro et al. |
| 5,425,382 A | 6/1995 | Golden et al. |
| 5,426,683 A | 6/1995 | O'Farrell, Jr. et al. |
| 5,426,687 A | 6/1995 | Goodall et al. |
| 5,427,097 A | 6/1995 | Depp |
| 5,429,132 A | 7/1995 | Guy et al. |
| 5,433,198 A | 7/1995 | Desai |
| RE35,025 E | 8/1995 | Anderton |
| 5,437,277 A | 8/1995 | Dumoulin et al. |
| 5,441,042 A * | 8/1995 | Putman ................ 600/102 |
| 5,443,066 A | 8/1995 | Dumoulin et al. |
| 5,443,489 A | 8/1995 | Ben-Haim |
| 5,444,756 A | 8/1995 | Pai et al. |
| 5,445,144 A | 8/1995 | Wodicka et al. |
| 5,445,150 A | 8/1995 | Dumoulin et al. |
| 5,445,166 A | 8/1995 | Taylor |
| 5,446,548 A | 8/1995 | Gerig et al. |
| 5,447,154 A | 9/1995 | Cinquin et al. |
| 5,448,610 A | 9/1995 | Yamamoto et al. |
| 5,453,686 A | 9/1995 | Anderson |
| 5,456,718 A | 10/1995 | Szymaitis |
| 5,457,641 A | 10/1995 | Zimmer et al. |
| 5,458,718 A | 10/1995 | Venkitachalam |
| 5,464,446 A | 11/1995 | Dreessen et al. |
| 5,469,847 A | 11/1995 | Zinreich et al. |
| 5,478,341 A | 12/1995 | Cook et al. |
| 5,478,343 A | 12/1995 | Ritter |
| 5,480,422 A | 1/1996 | Ben-Haim |
| 5,480,439 A | 1/1996 | Bisek et al. |
| 5,483,961 A | 1/1996 | Kelly et al. |
| 5,485,849 A | 1/1996 | Panescu et al. |
| 5,487,391 A | 1/1996 | Panescu |
| 5,487,729 A | 1/1996 | Avellanet et al. |
| 5,487,757 A | 1/1996 | Truckai et al. |
| 5,489,256 A | 2/1996 | Adair |

(56) References Cited

U.S. PATENT DOCUMENTS

| | | |
|---|---|---|
| 5,490,196 A | 2/1996 | Rudich et al. |
| 5,494,034 A | 2/1996 | Schlondorff et al. |
| 5,503,416 A | 4/1996 | Aoki et al. |
| 5,513,637 A | 5/1996 | Twiss et al. |
| 5,514,146 A | 5/1996 | Lam et al. |
| 5,515,160 A | 5/1996 | Schulz et al. |
| 5,517,990 A | 5/1996 | Kalfas et al. |
| 5,522,815 A | 6/1996 | Durgin, Jr. et al. |
| 5,531,227 A | 7/1996 | Schneider |
| 5,531,520 A | 7/1996 | Grimson et al. |
| 5,542,938 A | 8/1996 | Avellanet et al. |
| 5,543,951 A | 8/1996 | Moehrmann |
| 5,546,940 A | 8/1996 | Panescu et al. |
| 5,546,949 A | 8/1996 | Frazin et al. |
| 5,546,951 A | 8/1996 | Ben-Haim |
| 5,551,429 A | 9/1996 | Fitzpatrick et al. |
| 5,558,091 A | 9/1996 | Acker et al. |
| 5,566,681 A | 10/1996 | Manwaring et al. |
| 5,568,384 A | 10/1996 | Robb et al. |
| 5,568,809 A | 10/1996 | Ben-haim |
| 5,571,083 A | 11/1996 | Lemelson |
| 5,572,999 A | 11/1996 | Funda et al. |
| 5,573,533 A | 11/1996 | Strul |
| 5,575,794 A | 11/1996 | Walus et al. |
| 5,575,798 A | 11/1996 | Koutrouvelis |
| 5,577,991 A | 11/1996 | Akui et al. |
| 5,583,909 A | 12/1996 | Hanover |
| 5,588,430 A | 12/1996 | Bova et al. |
| 5,590,215 A | 12/1996 | Allen |
| 5,592,939 A | 1/1997 | Martinelli |
| 5,595,193 A | 1/1997 | Walus et al. |
| 5,596,228 A | 1/1997 | Anderton et al. |
| 5,600,330 A | 2/1997 | Blood |
| 5,603,318 A | 2/1997 | Heilbrun et al. |
| 5,611,025 A | 3/1997 | Lorensen et al. |
| 5,617,462 A | 4/1997 | Spratt |
| 5,617,857 A | 4/1997 | Chader et al. |
| 5,619,261 A | 4/1997 | Anderton |
| 5,622,169 A | 4/1997 | Golden et al. |
| 5,622,170 A | 4/1997 | Schulz |
| 5,627,873 A | 5/1997 | Hanover et al. |
| 5,628,315 A | 5/1997 | Vilsmeier et al. |
| 5,630,431 A | 5/1997 | Taylor |
| 5,636,644 A | 6/1997 | Hart et al. |
| 5,638,819 A | 6/1997 | Manwaring et al. |
| 5,640,170 A | 6/1997 | Anderson |
| 5,642,395 A | 6/1997 | Anderton et al. |
| 5,643,175 A | 7/1997 | Adair |
| 5,643,268 A | 7/1997 | Vilsmeier et al. |
| 5,645,065 A | 7/1997 | Shapiro et al. |
| 5,646,524 A | 7/1997 | Gilboa |
| 5,647,361 A | 7/1997 | Damadian |
| 5,662,111 A | 9/1997 | Cosman |
| 5,664,001 A | 9/1997 | Tachibana et al. |
| 5,674,296 A | 10/1997 | Bryan et al. |
| 5,676,673 A | 10/1997 | Ferre et al. |
| 5,681,260 A | 10/1997 | Ueda et al. |
| 5,682,886 A | 11/1997 | Delp et al. |
| 5,682,890 A | 11/1997 | Kormos et al. |
| 5,690,108 A | 11/1997 | Chakeres |
| 5,694,945 A | 12/1997 | Ben-Haim |
| 5,695,500 A | 12/1997 | Taylor et al. |
| 5,695,501 A | 12/1997 | Carol et al. |
| 5,696,500 A | 12/1997 | Diem |
| 5,697,377 A | 12/1997 | Wittkampf |
| 5,702,406 A | 12/1997 | Vilsmeier et al. |
| 5,711,299 A | 1/1998 | Manwaring et al. |
| 5,713,853 A | 2/1998 | Clark et al. |
| 5,713,946 A | 2/1998 | Ben-Haim |
| 5,715,822 A | 2/1998 | Watkins et al. |
| 5,715,836 A | 2/1998 | Kliegis et al. |
| 5,718,241 A | 2/1998 | Ben-Haim et al. |
| 5,727,552 A | 3/1998 | Ryan |
| 5,727,553 A | 3/1998 | Saad |
| 5,729,129 A | 3/1998 | Acker |
| 5,730,129 A | 3/1998 | Darrow et al. |
| 5,730,130 A | 3/1998 | Fitzpatrick et al. |
| 5,732,703 A | 3/1998 | Kalfas et al. |
| 5,735,278 A | 4/1998 | Hoult et al. |
| 5,738,096 A | 4/1998 | Ben-Haim |
| 5,740,802 A | 4/1998 | Nafis et al. |
| 5,741,214 A | 4/1998 | Ouchi et al. |
| 5,742,394 A | 4/1998 | Hansen |
| 5,744,953 A | 4/1998 | Hansen |
| 5,748,767 A | 5/1998 | Raab |
| 5,749,362 A | 5/1998 | Funda et al. |
| 5,749,835 A | 5/1998 | Glantz |
| 5,752,513 A | 5/1998 | Acker et al. |
| 5,755,725 A | 5/1998 | Druais |
| RE35,816 E | 6/1998 | Schulz |
| 5,758,667 A | 6/1998 | Slettenmark |
| 5,762,064 A | 6/1998 | Polyani |
| 5,767,669 A | 6/1998 | Hansen et al. |
| 5,767,699 A | 6/1998 | Bosnyak et al. |
| 5,767,960 A | 6/1998 | Orman |
| 5,769,789 A | 6/1998 | Wang et al. |
| 5,769,843 A | 6/1998 | Abela et al. |
| 5,769,861 A | 6/1998 | Vilsmeier |
| 5,772,594 A | 6/1998 | Barrick |
| 5,775,322 A | 7/1998 | Silverstein et al. |
| 5,776,064 A | 7/1998 | Kalfas et al. |
| 5,782,765 A | 7/1998 | Jonkman |
| 5,787,886 A | 8/1998 | Kelly et al. |
| 5,792,055 A | 8/1998 | McKinnon |
| 5,795,294 A | 8/1998 | Luber et al. |
| 5,797,849 A | 8/1998 | Vesely et al. |
| 5,799,055 A | 8/1998 | Peshkin et al. |
| 5,799,099 A | 8/1998 | Wang et al. |
| 5,800,352 A | 9/1998 | Ferre et al. |
| 5,800,535 A | 9/1998 | Howard, III |
| 5,802,719 A | 9/1998 | O'Farrell, Jr. et al. |
| 5,803,089 A | 9/1998 | Ferre et al. |
| 5,807,252 A | 9/1998 | Hassfeld et al. |
| 5,810,008 A | 9/1998 | Dekel et al. |
| 5,810,728 A | 9/1998 | Kuhn |
| 5,810,735 A | 9/1998 | Halperin et al. |
| 5,820,553 A | 10/1998 | Hughes |
| 5,823,192 A | 10/1998 | Kalend et al. |
| 5,823,958 A | 10/1998 | Truppe |
| 5,828,725 A | 10/1998 | Levinson |
| 5,828,770 A | 10/1998 | Leis et al. |
| 5,829,444 A | 11/1998 | Ferre et al. |
| 5,831,260 A | 11/1998 | Hansen |
| 5,833,608 A | 11/1998 | Acker |
| 5,834,759 A | 11/1998 | Glossop |
| 5,836,954 A | 11/1998 | Heilbrun et al. |
| 5,840,024 A | 11/1998 | Taniguchi et al. |
| 5,840,025 A | 11/1998 | Ben-Haim |
| 5,843,051 A | 12/1998 | Adams et al. |
| 5,843,076 A | 12/1998 | Webster, Jr. et al. |
| 5,846,183 A | 12/1998 | Chilcoat |
| 5,848,967 A | 12/1998 | Cosman |
| 5,851,183 A | 12/1998 | Bucholz |
| 5,865,726 A | 2/1999 | Katsurada et al. |
| 5,865,846 A | 2/1999 | Bryan et al. |
| 5,868,674 A | 2/1999 | Glowinski et al. |
| 5,868,675 A | 2/1999 | Henrion et al. |
| 5,871,445 A | 2/1999 | Bucholz |
| 5,871,455 A | 2/1999 | Ueno |
| 5,871,487 A | 2/1999 | Warner et al. |
| 5,873,822 A | 2/1999 | Ferre et al. |
| 5,882,304 A | 3/1999 | Ehnholm et al. |
| 5,884,410 A | 3/1999 | Prinz |
| 5,889,834 A | 3/1999 | Vilsmeier et al. |
| 5,891,034 A | 4/1999 | Bucholz |
| 5,891,157 A | 4/1999 | Day et al. |
| 5,904,691 A | 5/1999 | Barnett et al. |
| 5,907,395 A | 5/1999 | Schulz et al. |
| 5,913,820 A | 6/1999 | Bladen et al. |
| 5,920,395 A | 7/1999 | Schulz |
| 5,921,992 A | 7/1999 | Costales et al. |
| 5,923,727 A | 7/1999 | Navab |
| 5,928,248 A | 7/1999 | Acker |
| 5,935,160 A | 8/1999 | Auricchio et al. |

(56) References Cited

U.S. PATENT DOCUMENTS

| | | | |
|---|---|---|---|
| 5,938,585 A | 8/1999 | Donofrio |
| 5,938,603 A | 8/1999 | Ponzi |
| 5,938,694 A | 8/1999 | Jaraczewski et al. |
| 5,947,925 A | 9/1999 | Ashiya et al. |
| 5,947,980 A | 9/1999 | Jensen et al. |
| 5,947,981 A | 9/1999 | Cosman |
| 5,950,629 A | 9/1999 | Taylor et al. |
| 5,951,475 A | 9/1999 | Gueziec et al. |
| 5,951,571 A | 9/1999 | Audette |
| 5,954,647 A | 9/1999 | Bova et al. |
| 5,954,796 A | 9/1999 | McCarty et al. |
| 5,957,844 A | 9/1999 | Dekel et al. |
| 5,967,980 A | 10/1999 | Ferre et al. |
| 5,967,982 A | 10/1999 | Barnett |
| 5,968,047 A | 10/1999 | Reed |
| 5,971,997 A | 10/1999 | Guthrie et al. |
| 5,976,156 A | 11/1999 | Taylor et al. |
| 5,980,535 A | 11/1999 | Barnett et al. |
| 5,983,126 A | 11/1999 | Wittkampf |
| 5,987,349 A | 11/1999 | Schulz |
| 5,987,960 A | 11/1999 | Messner et al. |
| 5,997,473 A * | 12/1999 | Taniguchi et al. ............ 600/117 |
| 5,999,837 A | 12/1999 | Messner et al. |
| 5,999,840 A | 12/1999 | Grimson et al. |
| 6,001,130 A | 12/1999 | Bryan et al. |
| 6,004,269 A | 12/1999 | Crowley et al. |
| 6,006,126 A | 12/1999 | Cosman |
| 6,006,127 A | 12/1999 | Van Der Brug et al. |
| 6,013,087 A | 1/2000 | Adams et al. |
| 6,014,580 A | 1/2000 | Blume et al. |
| 6,016,439 A | 1/2000 | Acker |
| 6,019,725 A | 2/2000 | Vesely et al. |
| 6,024,695 A | 2/2000 | Taylor et al. |
| 6,050,724 A | 4/2000 | Schmitz et al. |
| 6,059,718 A | 5/2000 | Taniguchi et al. |
| 6,063,022 A | 5/2000 | Ben-Haim |
| 6,071,288 A | 6/2000 | Carol et al. |
| 6,073,043 A | 6/2000 | Schneider |
| 6,076,008 A | 6/2000 | Bucholz |
| 6,096,050 A | 8/2000 | Audette |
| 6,104,944 A | 8/2000 | Martinelli |
| 6,112,111 A | 8/2000 | Glantz |
| 6,118,845 A | 9/2000 | Simon et al. |
| 6,122,538 A | 9/2000 | Sliwa, Jr. et al. |
| 6,122,541 A | 9/2000 | Cosman et al. |
| 6,131,396 A | 10/2000 | Duerr et al. |
| 6,139,183 A | 10/2000 | Graumann |
| 6,147,480 A | 11/2000 | Osadchy et al. |
| 6,149,592 A | 11/2000 | Yanof et al. |
| 6,156,067 A | 12/2000 | Bryan et al. |
| 6,161,032 A | 12/2000 | Acker |
| 6,165,181 A | 12/2000 | Heilbrun et al. |
| 6,167,296 A | 12/2000 | Shahidi |
| 6,172,499 B1 | 1/2001 | Ashe |
| 6,175,756 B1 | 1/2001 | Ferre et al. |
| 6,178,345 B1 | 1/2001 | Vilsmeier et al. |
| 6,183,444 B1 | 2/2001 | Glines et al. |
| 6,188,355 B1 | 2/2001 | Gilboa |
| 6,192,280 B1 | 2/2001 | Sommer et al. |
| 6,194,639 B1 | 2/2001 | Botella et al. |
| 6,196,966 B1 | 3/2001 | Kerin et al. |
| 6,201,387 B1 | 3/2001 | Govari |
| 6,203,493 B1 | 3/2001 | Ben-Haim |
| 6,203,497 B1 | 3/2001 | Dekel et al. |
| 6,203,533 B1 * | 3/2001 | Ouchi ............................ 604/264 |
| 6,210,362 B1 | 4/2001 | Ponzi |
| 6,211,666 B1 | 4/2001 | Acker |
| 6,213,995 B1 | 4/2001 | Steen et al. |
| 6,216,027 B1 | 4/2001 | Willis et al. |
| 6,223,067 B1 | 4/2001 | Vilsmeier |
| 6,226,543 B1 | 5/2001 | Gilboa et al. |
| 6,233,476 B1 | 5/2001 | Strommer et al. |
| 6,236,875 B1 | 5/2001 | Bucholz et al. |
| 6,246,231 B1 | 6/2001 | Ashe |
| 6,253,770 B1 | 7/2001 | Acker et al. |
| 6,259,942 B1 | 7/2001 | Westermann et al. |
| 6,273,896 B1 | 8/2001 | Franck et al. |
| 6,285,902 B1 | 9/2001 | Kienzle, III et al. |
| 6,298,262 B1 | 10/2001 | Franck et al. |
| 6,314,310 B1 | 11/2001 | Ben-Haim et al. |
| 6,331,156 B1 | 12/2001 | Haefele et al. |
| 6,332,089 B1 | 12/2001 | Acker et al. |
| 6,335,617 B1 | 1/2002 | Osadchy et al. |
| 6,341,231 B1 | 1/2002 | Ferre et al. |
| 6,351,659 B1 | 2/2002 | Vilsmeier |
| 6,366,799 B1 | 4/2002 | Acker et al. |
| 6,373,240 B1 | 4/2002 | Govari |
| 6,381,485 B1 | 4/2002 | Hunter et al. |
| 6,423,009 B1 | 7/2002 | Downey et al. |
| 6,424,856 B1 | 7/2002 | Vilsmeier et al. |
| 6,427,314 B1 | 8/2002 | Acker |
| 6,428,547 B1 | 8/2002 | Vilsmeier et al. |
| 6,434,415 B1 | 8/2002 | Foley et al. |
| 6,437,567 B1 | 8/2002 | Schenck et al. |
| 6,440,061 B1 | 8/2002 | Wenner et al. |
| 6,445,943 B1 | 9/2002 | Ferre et al. |
| 6,447,504 B1 | 9/2002 | Ben-Haim et al. |
| 6,453,190 B1 | 9/2002 | Acker et al. |
| 6,470,207 B1 | 10/2002 | Simon et al. |
| 6,474,341 B1 | 11/2002 | Hunter et al. |
| 6,478,802 B2 | 11/2002 | Kienzle, III et al. |
| 6,484,049 B1 | 11/2002 | Seeley et al. |
| 6,484,118 B1 | 11/2002 | Govari |
| 6,490,475 B1 | 12/2002 | Seeley et al. |
| 6,493,573 B1 | 12/2002 | Martinelli et al. |
| 6,498,944 B1 | 12/2002 | Ben-Haim et al. |
| 6,499,488 B1 | 12/2002 | Hunter et al. |
| 6,516,046 B1 | 2/2003 | Frohlich et al. |
| 6,527,443 B1 | 3/2003 | Vilsmeier et al. |
| 6,551,325 B2 | 4/2003 | Neubauer et al. |
| 6,580,938 B1 | 6/2003 | Acker |
| 6,584,174 B2 | 6/2003 | Schubert et al. |
| 6,591,129 B1 | 7/2003 | Ben-Haim et al. |
| 6,593,884 B1 | 7/2003 | Gilboa et al. |
| 6,609,022 B2 | 8/2003 | Vilsmeier et al. |
| 6,611,700 B1 | 8/2003 | Vilsmeier et al. |
| 6,612,992 B1 | 9/2003 | Hossack et al. |
| 6,618,612 B1 | 9/2003 | Acker et al. |
| 6,640,128 B2 | 10/2003 | Vilsmeier et al. |
| 6,650,927 B1 | 11/2003 | Keidar |
| 6,690,963 B2 | 2/2004 | Ben-Haim et al. |
| 6,694,162 B2 | 2/2004 | Hartlep |
| 6,701,179 B1 | 3/2004 | Martinelli et al. |
| 6,711,429 B1 | 3/2004 | Gilboa et al. |
| 6,788,967 B2 | 9/2004 | Ben-Haim et al. |
| 6,796,939 B1 | 9/2004 | Hirata et al. |
| 6,942,613 B2 | 9/2005 | Ewers et al. |
| 6,962,565 B2 | 11/2005 | Nakamura |
| 6,995,729 B2 | 2/2006 | Govari et al. |
| 7,068,825 B2 | 6/2006 | Rubbert et al. |
| 7,197,354 B2 | 3/2007 | Sobe |
| 7,233,820 B2 | 6/2007 | Gilboa |
| 7,236,567 B2 | 6/2007 | Sandkamp et al. |
| 7,286,868 B2 | 10/2007 | Govari |
| 7,301,332 B2 | 11/2007 | Govari et al. |
| 7,321,228 B2 | 1/2008 | Govari |
| 7,324,915 B2 | 1/2008 | Altmann et al. |
| 7,343,195 B2 | 3/2008 | Strommer et al. |
| 7,353,125 B2 | 4/2008 | Nieminen et al. |
| 7,357,795 B2 | 4/2008 | Kaji et al. |
| 7,366,562 B2 | 4/2008 | Dukesherer et al. |
| 7,370,656 B2 | 5/2008 | Gleich et al. |
| 7,373,271 B1 | 5/2008 | Schneider |
| 7,386,339 B2 | 6/2008 | Strommer et al. |
| 7,397,364 B2 | 7/2008 | Govari |
| 7,399,296 B2 | 7/2008 | Poole et al. |
| 7,497,029 B2 | 3/2009 | Plassky et al. |
| 7,505,809 B2 | 3/2009 | Strommer et al. |
| 7,536,218 B2 | 5/2009 | Govari et al. |
| RE40,852 E | 7/2009 | Martinelli et al. |
| 7,570,987 B2 | 8/2009 | Raabe et al. |
| 7,577,474 B2 | 8/2009 | Vilsmeier |
| 7,579,837 B2 | 8/2009 | Fath et al. |
| 7,587,235 B2 | 9/2009 | Wist et al. |

(56) References Cited

U.S. PATENT DOCUMENTS

| | | |
|---|---|---|
| 7,599,535 B2 | 10/2009 | Kiraly et al. |
| 7,599,810 B2 | 10/2009 | Yamazaki |
| 7,630,753 B2 | 12/2009 | Simon et al. |
| 7,634,122 B2 | 12/2009 | Bertram et al. |
| 7,636,595 B2 | 12/2009 | Marquart et al. |
| 7,641,609 B2 | 1/2010 | Ohnishi et al. |
| 7,648,458 B2 | 1/2010 | Niwa et al. |
| 7,652,468 B2 | 1/2010 | Kruger et al. |
| 7,657,300 B2 | 2/2010 | Hunter et al. |
| 7,659,912 B2 | 2/2010 | Akimoto et al. |
| 7,660,623 B2 | 2/2010 | Hunter et al. |
| 7,680,528 B2 | 3/2010 | Pfister et al. |
| 7,684,849 B2 | 3/2010 | Wright et al. |
| 7,686,767 B2 | 3/2010 | Maschke |
| 7,688,064 B2 | 3/2010 | Shalgi et al. |
| 7,696,899 B2 | 4/2010 | Immerz et al. |
| 7,697,972 B2 | 4/2010 | Verard et al. |
| 7,697,973 B2 | 4/2010 | Strommer et al. |
| 7,697,974 B2 | 4/2010 | Jenkins et al. |
| 7,720,517 B2 | 5/2010 | Drysen |
| 7,722,565 B2 | 5/2010 | Wood et al. |
| 7,725,154 B2 | 5/2010 | Beck et al. |
| 7,725,164 B2 | 5/2010 | Suurmond et al. |
| 7,727,269 B2 | 6/2010 | Abraham-Fuchs et al. |
| 7,729,742 B2 | 6/2010 | Govari |
| 7,744,605 B2 | 6/2010 | Vilsmeier et al. |
| 7,747,307 B2 | 6/2010 | Wright et al. |
| 7,751,865 B2 | 7/2010 | Jascob et al. |
| 7,760,909 B2 | 7/2010 | Manus |
| 7,764,984 B2 | 7/2010 | Desmedt et al. |
| 7,774,045 B2 | 8/2010 | Ikuma et al. |
| 7,778,688 B2 | 8/2010 | Strommer |
| 7,778,689 B2 | 8/2010 | Boese et al. |
| 7,778,690 B2 | 8/2010 | Boese et al. |
| 7,783,441 B2 | 8/2010 | Nieminen et al. |
| 7,787,932 B2 | 8/2010 | Vilsmeier et al. |
| 7,788,060 B2 | 8/2010 | Schneider |
| 2001/0007918 A1 | 7/2001 | Vilsmeier et al. |
| 2001/0031919 A1 | 10/2001 | Strommer et al. |
| 2001/0034530 A1 | 10/2001 | Malackowsli et al. |
| 2001/0036245 A1 | 11/2001 | Kienzle, III et al. |
| 2002/0095081 A1 | 7/2002 | Vilsmeier |
| 2002/0128565 A1 | 9/2002 | Rudy |
| 2002/0173689 A1 | 11/2002 | Kaplan |
| 2002/0193686 A1 | 12/2002 | Gilboa |
| 2003/0018251 A1 | 1/2003 | Solomon |
| 2003/0074011 A1 | 4/2003 | Gilboa et al. |
| 2003/0086599 A1 | 5/2003 | Armato et al. |
| 2003/0142753 A1 | 7/2003 | Gunday |
| 2003/0160721 A1 | 8/2003 | Gilboa et al. |
| 2004/0015049 A1 | 1/2004 | Zaar |
| 2004/0024309 A1 | 2/2004 | Ferre et al. |
| 2004/0086161 A1 | 5/2004 | Sivaramakrishna et al. |
| 2004/0097804 A1* | 5/2004 | Sobe ................... 600/424 |
| 2004/0138548 A1 | 7/2004 | Strommer et al. |
| 2004/0169509 A1 | 9/2004 | Czipott et al. |
| 2004/0249267 A1 | 12/2004 | Gilboa |
| 2005/0033149 A1 | 2/2005 | Strommer et al. |
| 2005/0085715 A1 | 4/2005 | Dukesher et al. |
| 2005/0107688 A1 | 5/2005 | Strommer |
| 2005/0119527 A1 | 6/2005 | Banik et al. |
| 2005/0197566 A1 | 9/2005 | Strommer et al. |
| 2005/0272975 A1* | 12/2005 | McWeeney et al. ......... 600/113 |
| 2006/0015126 A1 | 1/2006 | Sher |
| 2006/0058647 A1 | 3/2006 | Strommer et al. |
| 2006/0064006 A1 | 3/2006 | Strommer et al. |
| 2006/0149134 A1 | 7/2006 | Soper et al. |
| 2007/0163597 A1 | 7/2007 | Mikkaichi et al. |
| 2007/0167714 A1 | 7/2007 | Kiraly et al. |
| 2007/0167738 A1 | 7/2007 | Timinger et al. |
| 2007/0167743 A1 | 7/2007 | Honda et al. |
| 2007/0167806 A1 | 7/2007 | Wood et al. |
| 2007/0265639 A1 | 11/2007 | Danek et al. |
| 2007/0287901 A1 | 12/2007 | Strommer et al. |
| 2008/0086051 A1 | 4/2008 | Voegele |
| 2008/0097187 A1 | 4/2008 | Gielen et al. |
| 2008/0118135 A1 | 5/2008 | Averbuch et al. |
| 2008/0132909 A1 | 6/2008 | Jascob et al. |
| 2008/0132911 A1 | 6/2008 | Sobe |
| 2008/0139886 A1 | 6/2008 | Tatsuyama |
| 2008/0139915 A1 | 6/2008 | Dolan et al. |
| 2008/0144909 A1 | 6/2008 | Wiemker et al. |
| 2008/0147000 A1 | 6/2008 | Seibel et al. |
| 2008/0154172 A1 | 6/2008 | Mauch |
| 2008/0157755 A1 | 7/2008 | Kruger et al. |
| 2008/0161682 A1 | 7/2008 | Kendrick et al. |
| 2008/0162074 A1 | 7/2008 | Schneider |
| 2008/0183071 A1 | 7/2008 | Strommer et al. |
| 2008/0188749 A1 | 8/2008 | Rasche et al. |
| 2009/0182224 A1 | 7/2009 | Shmarak et al. |

FOREIGN PATENT DOCUMENTS

| | | |
|---|---|---|
| DE | 35 08 730 A1 | 9/1986 |
| DE | 35 20 782 A1 | 12/1986 |
| DE | 37 17 871 A1 | 12/1988 |
| DE | 38 31 278 A1 | 3/1989 |
| DE | 38 38 011 A1 | 7/1989 |
| DE | 42 13 426 A1 | 10/1992 |
| DE | 42 25 112 C1 | 12/1993 |
| DE | 42 33 978 C1 | 4/1994 |
| DE | 197 15 202 A1 | 10/1998 |
| DE | 197 51 761 A1 | 10/1998 |
| DE | 198 32 296 A1 | 2/1999 |
| DE | 197 47 427 A1 | 5/1999 |
| DE | 100 85 137 T1 | 11/2002 |
| EP | 0 062 941 A1 | 10/1982 |
| EP | 0 119 660 A1 | 9/1984 |
| EP | 0 155 857 A2 | 9/1985 |
| EP | 0 319 844 A1 | 6/1989 |
| EP | 0 326 768 A2 | 8/1989 |
| EP | 0 350 996 A1 | 1/1990 |
| EP | 350996 A1 | 1/1990 |
| EP | 0 419 729 A1 | 4/1991 |
| EP | 0 427 358 A1 | 5/1991 |
| EP | 0 456 103 A2 | 11/1991 |
| EP | 0 581 704 A1 | 2/1994 |
| EP | 0 894 473 A2 | 8/1994 |
| EP | 0 651 968 A1 | 5/1995 |
| EP | 0 796 633 A1 | 9/1997 |
| EP | 0 908 146 A2 | 10/1997 |
| EP | 0 930 046 A2 | 11/1997 |
| EP | 0 655 138 B1 | 4/1998 |
| EP | 1 078 644 A1 | 8/1999 |
| FR | 2 417 970 A1 | 9/1979 |
| FR | 2 618 211 A1 | 1/1989 |
| GB | 2 094 590 A | 9/1982 |
| GB | 2 164 856 A | 4/1986 |
| JP | 6 3240851 A | 10/1988 |
| JP | 03 267054 A | 11/1991 |
| JP | 06 194639 A | 7/1994 |
| JP | 09-253038 | 9/1997 |
| JP | 2001-231743 | 8/2001 |
| JP | 2001-275942 | 10/2001 |
| WO | WO 88/09151 A1 | 12/1988 |
| WO | WO 89/05123 A1 | 6/1989 |
| WO | WO 90/05494 A1 | 5/1990 |
| WO | WO 91/03982 A1 | 4/1991 |
| WO | WO 91/04711 A1 | 4/1991 |
| WO | WO 91/07726 A1 | 5/1991 |
| WO | WO 92/03090 A1 | 3/1992 |
| WO | WO 92/06645 A1 | 4/1992 |
| WO | WO 94/04938 A1 | 3/1994 |
| WO | WO 94/23647 A1 | 10/1994 |
| WO | WO 94/24933 A1 | 11/1994 |
| WO | WO 95/07055 A1 | 3/1995 |
| WO | WO 96/11624 A1 | 4/1996 |
| WO | WO 96/32059 A1 | 10/1996 |
| WO | WO 97/36192 A1 | 10/1997 |
| WO | WO 97/49453 A1 | 12/1997 |
| WO | WO 98/08554 A1 | 3/1998 |

(56) References Cited

FOREIGN PATENT DOCUMENTS

| | | |
|---|---|---|
| WO | WO 98/38908 A1 | 9/1998 |
| WO | WO 99/15097 A1 | 4/1999 |
| WO | WO 99/21498 A1 | 5/1999 |
| WO | WO 99/23956 A1 | 5/1999 |
| WO | WO 99/26549 A1 | 6/1999 |
| WO | WO 99/27839 A1 | 6/1999 |
| WO | WO 99/29253 A1 | 6/1999 |
| WO | WO 99/33406 A1 | 7/1999 |
| WO | WO 99/37208 A1 | 7/1999 |
| WO | WO 99/38449 A1 | 8/1999 |
| WO | WO 99/52094 A1 | 10/1999 |
| WO | WO 99/60939 A1 | 12/1999 |
| WO | WO 00/06701 A1 | 2/2000 |
| WO | WO 00/35531 A1 | 6/2000 |
| WO | WO 01/30437 A1 | 5/2001 |
| WO | WO 02/070047 A1 | 9/2001 |
| WO | WO 01/87136 A2 | 11/2001 |
| WO | WO 01/91842 | 12/2001 |
| WO | WO 02/064011 A2 | 8/2002 |
| WO | WO 2004/023986 A1 | 3/2004 |

OTHER PUBLICATIONS

United States Patent and Trademark Office, Office Action mailed Oct. 18, 2010 in U.S. Appl. No. 11/765,330, 35 pages.
United States Patent and Trademark Office, Notice of Allowance mailed Oct. 6, 2006 in U.S. Appl. No. 10/491,099, 7 pages.
United States Patent and Trademark Office, Office Action mailed Dec. 30, 2005 in U.S. Appl. No. 10/491,099, 14 pages.
United States Patent and Trademark Office, Office Action mailed Apr. 22, 2005 in U.S. Appl. No. 10/491,099, 5 pages.
EP Examination Report dated Jul. 14, 2009 in corresponding EP Application No. 03719056.8 (6 pgs.).
European Search Report dated Sep. 6, 2011 in corresponding EP Application No. 11174666.5 (6 pgs.).
EP Examination Report dated Aug. 11, 2010 in corresponding EP Application No. 03719056.9 ((4 pgs.).
Official Action dated Dec. 18, 2009 in corresponding JP Application No. 2003-583508 (4 pgs.)
Official Action dated Dec. 12, 2008 in corresponding JP Application No. 2003-583508 (5 pgs.)

\* cited by examiner

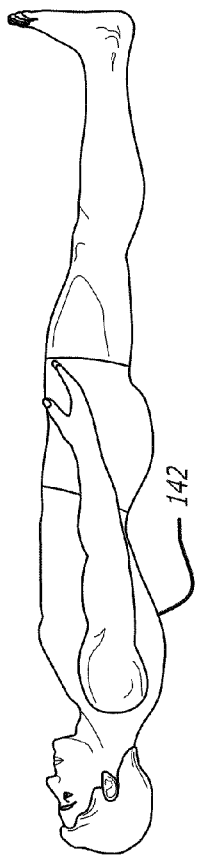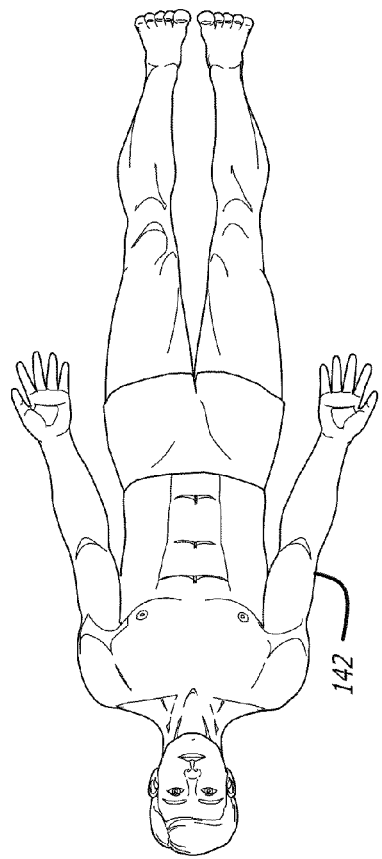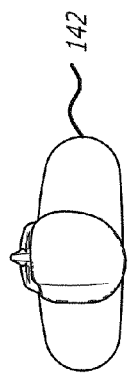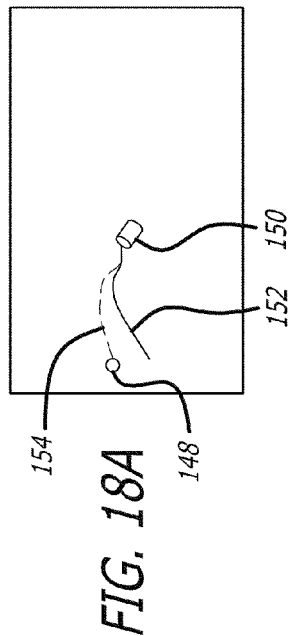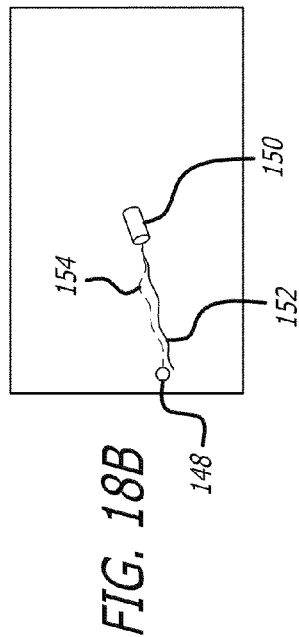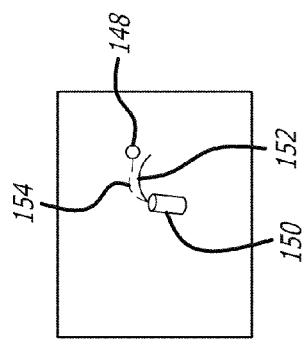
FIG. 18A  FIG. 18B  FIG. 18C

ENDOSCOPE STRUCTURES AND TECHNIQUES FOR NAVIGATING TO A TARGET IN BRANCHED STRUCTURE

The present invention is a divisional of U.S. patent application Ser. No. 11/765,330 filed Jun. 19, 2007 entitled Endoscope Structures And Techniques For Navigating To A Target In Branched Structure, now U.S. Pat. No. 7,998,062, which is a continuation of U.S. patent application Ser. No. 10/491,099 filed Mar. 29, 2004 entitled Endoscope Structures And Techniques For Navigating To A Target In Branched Structure, now U.S. Pat. No. 7,233,820; which claims benefit of International patent application no. PCT/IL03/00323, International Filing Date 16 Apr. 2003, entitled Endoscope Structures And Techniques For Navigating To A Target In Branched Structure, which claims benefit of U.S. Provisional Application Ser. No. 60/372,804, filed Apr. 17, 2002, U.S. Provisional Application Ser. No. 60/388,758, filed Jun. 17, 2002, and U.S. Provisional Application Ser. No. 60/407,951, filed Sep. 5, 2002, all of which are incorporated herein by reference.

FIELD AND BACKGROUND OF THE INVENTION

The present invention relates to endoscopes and, in particular, it concerns endoscope structures and techniques for navigating to a target in branched structure, such as the human lungs, and for bringing a medical tool to the target.

Biopsy taken from suspected malignant tissue inside the bronchial tree is conventionally performed using a bronchoscope. The bronchoscope, which is a type of endoscope, is a flexible tube having a miniature camera at its tip. Actuated from a handle at its proximal end, its tip has the ability to deflect in two opposite directions, allowing it to be steered inside the bronchial tree. The bronchoscope also has a working channel, typically of internal diameter about 2.8 mm, allowing a tool such as a biopsy forceps to be inserted and driven ahead of its distal tip.

Once unidentified lung mass is discovered in a CT scan, a biopsy of this mass should be taken. The patient is positioned on an operating table, a bronchoscope is inserted into the bronchial tree and directed towards the mass. Once the tip of the bronchoscope is placed in contact with the mass, as validated by direct viewing of the mass in the bronchoscope image, a forceps is pushed via the working channel into the mass and biopsy is taken.

While this technique is straightforward in principle, the practical application is often highly problematic. The air paths of the bronchial tree get progressively narrower as they branch with increasing depth into the bronchial tree. A typical bronchoscope is a two- or three-lumen structure (including fiber bundles for imaging and illumination and working channel for suction and/or tools) and is typically around 5 or 6 millimeters in diameter. In consequence, a bronchoscope can reach only the third, or at most the fourth, bifurcation level of the tree (indicated by a dashed circle in FIG. 24). If the mass is at the periphery of the tree, the biopsy forceps must be pushed further ahead of the tip of the bronchoscope in the estimated direction of the mass. The biopsy itself is then taken blindly. X-ray fluoroscopic imaging is often used as a visual aid, but this is only of any value for relatively large masses visible under a fluoroscope, and the two-dimensional images produced are a poor navigation aid, lacking depth perception. For these and other reasons, it is estimated that more than 60% of the total number of bronchial biopsies are taken mistakenly in a wrong location.

Various devices have been proposed in order to try to ameliorate the limitations of bronchoscopes. Of particular interest is U.S. Pat. No. 4,586,491 to Carpenter which discloses a bronchoscope with a small gauge viewing attachment. The viewing attachment is selectively advanced past the end of the bronchoscope to view tissue beyond the reach of the main bronchoscope shaft.

Although the device of Carpenter allows viewing of tissue within passageways too narrow for the bronchoscope to enter, it is very limited in its usefulness. Firstly, the viewing attachment is not steerable, relying instead on the pointing direction of the end of the bronchoscope. As a result, the viewing attachment is limited in its capabilities to reach target tissue. Secondly, the system provides no location information to facilitate navigation to the target tissue. Finally, the device is of little or no use for navigating a medical tool to the target location. If the viewing attachment is removed to allow introduction of a tool to the working channel, manipulation of the tool must again be performed "blindly" without any guarantee that the correct target tissue has been reached.

There is therefore a need for endoscopes and corresponding methods which facilitate navigation to a target within a branched structure such as the bronchial tree, and which allows a medical tool to be brought accurately to the target.

SUMMARY OF THE INVENTION

The present invention provides endoscope structures and corresponding techniques for navigating to a target in branched structure, such as the human lungs, and for bringing a medical tool to the target.

According to the teachings of the present invention there is provided, a method for steering a catheter through a branched structure to a target location, the method comprising: (a) providing a flexible, steerable catheter with a position sensor element located near a distal tip of the catheter, the position sensor element being part of a position measuring system measuring a position and a pointing direction of the tip of the catheter relative to a three-dimensional frame of reference; (b) designating the target location relative to the three-dimensional frame of reference; (c) advancing the catheter into the branched structure; and (d) displaying a representation of at least one parameter defined by a geometrical relation between the pointing direction of the tip of the catheter and a direction from the tip of the catheter towards the target location.

According to a further feature of the present invention, the at least one parameter includes an angular deviation between the pointing direction of the tip of the catheter and a direction from the tip of the catheter towards the target location.

According to a further feature of the present invention, the at least one parameter includes a direction of deflection required to bring the pointing direction of the catheter into alignment with the target location.

According to a further feature of the present invention, the representation of at least one parameter is displayed in the context of a representation of a view taken along the pointing direction of the tip of the catheter.

According to a further feature of the present invention, the position sensor element is part of a six-degrees-of-freedom position measuring system measuring the position and attitude of the tip of the catheter in three translational and three rotational degrees of freedom.

According to a further feature of the present invention, the catheter is further provided with a multi-directional steering mechanism configured for selectively deflecting a distal portion of the catheter in any one of at least three different directions.

According to a further feature of the present invention, a path traveled by the tip of the catheter is monitored by use of the position sensor element and a representation of the path traveled is displayed together with a current position of the tip, the representation being projected as viewed from at least one direction non-parallel to the pointing direction of the tip.

According to a further feature of the present invention, the designating the target location is performed by: (a) designating a target location by use of computerized tomography data generated from the branched structure; and (b) registering the computerized tomography data with the three-dimensional frame of reference.

According to a further feature of the present invention, the registering is performed by: (a) providing the steerable catheter with a camera; (b) generating a camera view of each of at least three distinctive features within the branched structure; (c) generating from the computerized tomography data a simulated view of each of the at least three distinctive features, each camera view and a corresponding one of the simulated views constituting a pair of similar views; (d) allowing an operator to designate a reference point viewed within each of the camera views and a corresponding reference point viewed within each corresponding simulated view; and (e) deriving from the designated reference points a best fit registration between the computerized tomography data and the three-dimensional frame of reference.

According to a further feature of the present invention, an intended route through the branched structure is designated by use of the computerized tomography data and a representation of the intended route is displayed together with a current position of the tip, the representation being projected as viewed from at least one direction non-parallel to the pointing direction of the tip.

According to a further feature of the present invention: (a) a current position of the position sensor element is detected; (b) a virtual endoscopy image is generated from the computerized tomography data corresponding to an image that would be viewed by a camera located in predefined spatial relationship and alignment relative to the position sensor element; and (c) displaying the virtual endoscopy image.

According to a further feature of the present invention, the branched structure is a lung structure.

According to a further feature of the present invention, measurements of the position and pointing direction of the tip of the catheter are processed so as to reduce variations resulting from cyclic motion.

According to a further feature of the present invention, the processing includes selectively taking measurements at an extreme of a cyclic motion.

According to a further feature of the present invention, the processing includes applying a low-frequency filter to the measurements.

According to a further feature of the present invention, the processing includes calculating an average of the measurements over a time period of the cyclic motion.

According to a further feature of the present invention, the steerable catheter further includes: a sheath having a lumen extending from a proximal insertion opening to a distal opening; and a guide element configured for insertion through the proximal opening of the sheath to an inserted position extending along the lumen to the distal opening, the guide element including at least part of an imaging system deployed for taking optical images of a region beyond the distal opening, the method further comprising: (a) guiding the steerable catheter to a position with the tip adjacent to the target location; and (b) withdrawing the guide element from the lumen to leave the lumen available for insertion of a medical tool.

According to a further feature of the present invention, a medical tool is prepared for insertion into the lumen by: (a) inserting the medical tool into a calibration tube, the calibration tube having a length corresponding to a length of the lumen; and (b) marking an extent of insertion on the tool.

According to a further feature of the present invention, the calibration tube is a coiled storage tube employed to store the guide element prior to use, the guide element being removed from the storage tube prior to inserting the tool.

According to a further feature of the present invention, the steerable catheter further includes a handle having a working channel, a sheath deployed within the working channel and having an internal lumen, and a guide element including the position sensor element deployed within the lumen, the method further comprising: (a) locking the guide element within the sheath so as to prevent movement of the guide element relative to the sheath; (b) guiding the sheath and the guide element to the target location; (c) locking the sheath within the working channel to prevent relative movement of the sheath relative to the handle; and (d) unlocking and withdrawing the guide element from the sheath so as to leave the lumen of the sheath in place as a guide for inserting a tool to the target location.

According to a further feature of the present invention, a selectively actuatable anchoring mechanism is associated with a portion of the sheath.

According to a further feature of the present invention, the selectively actuatable anchoring mechanism includes an inflatable element.

According to a further feature of the present invention, the selectively actuatable anchoring mechanism includes a mechanically deployed element.

According to a further feature of the present invention, the guide element further includes an image sensor deployed for generating an image in the pointing direction of the catheter, the image sensor being withdrawn from the sheath as part of the guide element.

According to a further feature of the present invention, at least part of the location sensor is formed from translucent material, the method further comprising illuminating at least part of a field of view of the image sensor by directing illumination through at least one region of the translucent material.

According to a further feature of the present invention, at least part of a field of view of the image sensor is illuminated by using at least a distal portion of the sheath as an optical waveguide.

According to a further feature of the present invention, illumination is supplied to the optical waveguide from at least one light source mounted within the guide element.

According to a further feature of the present invention, illumination is supplied to the optical waveguide from at least one light source associated with the handle.

According to a further feature of the present invention, the guide element further includes a radioactivity sensor, the sensor being withdrawn from the sheath as part of the guide element.

According to a further feature of the present invention, the steerable catheter is a flexible endoscope.

According to a further feature of the present invention, the steerable catheter is a flexible bronchoscope.

There is also provided according to the teachings of the present invention, a method for achieving registration between computerized tomography data and a three dimensional frame of reference of a position measuring system, the method comprising: (a) providing a catheter with: (i) a position sensor element which operates as part of the position measuring system to allow measurement of a position and a pointing direction of the tip of the catheter relative to the three-dimensional frame of reference, and (ii) an image sensor; (b) generating from the computerized tomography data at least three simulated views of distinctive features within the branched structure; (c) generating at least three camera views of the distinctive features, each camera view and a corresponding one of the simulated views constituting a pair of similar views; (d) allowing an operator to designate a reference point viewed within each of the camera views and a corresponding reference point viewed within each corresponding simulated view; and (e) deriving from the designated reference points a best fit registration between the computerized tomography image and the three-dimensional frame of reference.

According to a further feature of the present invention, designation of a reference point within each of the camera views by the operator is performed by the operator bringing the position sensor element into proximity with the reference point.

According to a further feature of the present invention, designation of a reference point within each simulated view by the operator is performed by: (a) the operator selecting a simulated image reference point within each simulated view; (b) calculating from the simulated image reference point a simulated-viewing-point-to-reference-point vector; and (c) calculating a point of intersection between the simulated-viewing-point-to-reference-point vector and a tissue surface in a numerical model of a portion of the body derived from the computerized tomography data.

According to a further feature of the present invention: (a) at least one location within the computerized tomography data is identified; (b) a position of the at least one location is calculated within the three-dimensional frame of reference; and (c) a representation of the at least one location is displayed together with a representation of a position of the position sensor element.

According to a further feature of the present invention, the at least one location includes a target location to which a medical tool is to be directed.

According to a further feature of the present invention, the at least one location is a series of locations defining a planned path along which a medical tool is to be directed.

There is also provided according to the teachings of the present invention, a method for achieving registration between computerized tomography data and a three dimensional frame of reference of a position measuring system, the method comprising: (a) providing a catheter with: (i) a position sensor element which operates as part of the position measuring system to allow measurement of a position and a pointing direction of the tip of the catheter relative to the three-dimensional frame of reference, and (ii) an image sensor; (b) moving the tip of the catheter along a first branch portion of a branched structure and deriving a plurality of images from the camera, each image being associated with corresponding position data of the position sensor in the three dimensional frame of reference; (c) processing the images and corresponding position data to derive a best-fit of a predefined geometrical model to the first branch portion in the three dimensional frame of reference; (d) repeating steps (b) and (c) for a second branch portion of the branched structure; and (e) correlating the geometrical models of the first and second branch portions with the computerized tomography data to derive a best fit registration between the computerized tomography data and the three dimensional frame of reference.

According to a further feature of the present invention, the processing the images and corresponding position data includes: (a) identifying visible features each of which is present in plural images taken at different positions; (b) for each of the visible features, deriving a camera-to-feature direction in each of a plurality of the images; (c) employing the camera-to-feature directions and corresponding position data to determine a feature position for each visible feature; and (d) deriving a best-fit of the predefined geometrical model to the feature positions.

According to a further feature of the present invention, the predefined geometrical model is a cylinder.

According to a further feature of the present invention: (a) at least one location within the computerized tomography data is identified; (b) a position of the at least one location within the three-dimensional frame of reference is calculated; and (c) a representation of the at least one location is displayed together with a representation of a position of the position sensor element.

According to a further feature of the present invention, the at least one location includes a target location to which a medical tool is to be directed.

According to a further feature of the present invention, the at least one location is a series of locations defining a planned path along which a medical tool is to be directed.

There is also provided according to the teachings of the present invention, an endoscope for guiding a medical tool to a target location, the endoscope comprising: (a) a sheath having a lumen extending from a proximal insertion opening to a distal opening; (b) a guide element configured for insertion through the proximal opening of the sheath to an inserted position extending along the lumen to the distal opening, the guide element including at least part of an imaging system deployed for taking optical images of a region beyond the distal opening; and (c) at least one steering mechanism for co-deflecting the sheath and the guide element, wherein the guide element is retractable from the lumen to leave the lumen available for insertion of a medical tool.

According to a further feature of the present invention, the at least part of an imaging system includes an optical sensor chip deployed at a distal end of the guide element.

According to a further feature of the present invention, the guide element includes a position sensor element, the position sensor element being part of a position measuring system measuring a position and a pointing direction of a tip of the guide element relative to a three-dimensional frame of reference.

According to a further feature of the present invention, at least part of the position sensor element is formed from translucent material, the endoscope further comprising an illumination arrangement deployed to direct illumination through at least one region of the translucent material so as to illuminate at least part of the region beyond the distal opening.

According to a further feature of the present invention, there is also provided a selectively actuatable anchoring mechanism associated with a portion of the sheath.

According to a further feature of the present invention, the selectively actuatable anchoring mechanism includes an inflatable element.

According to a further feature of the present invention, the selectively actuatable anchoring mechanism includes a mechanically deployed element.

According to a further feature of the present invention, at least a distal part of the sheath is substantially radio-opaque.

According to a further feature of the present invention, there is also provided at least one radio-opaque marked associated with a distal end of the sheath.

According to a further feature of the present invention, at least a distal portion of the sheath is implemented as an optical waveguide.

According to a further feature of the present invention, there is also provided at least one light source mounted within the guide element for illuminating at least part of the region beyond the distal opening.

According to a further feature of the present invention, there is also provided at least one optical fiber deployed along the length of the guide element for delivering illumination to at least part of the region beyond the distal opening.

According to a further feature of the present invention, the guide element further includes a radioactivity sensor, the sensor being withdrawn from the sheath as part of the guide element.

There is also provided according to the teachings of the present invention, a method of guiding a medical tool through a branched structure to a target location, the method comprising: (a) providing a catheter assembly including a handle having a working channel, a sheath deployed within the working channel and having an internal lumen, and a guide element deployed within the lumen; (b) locking the guide element within the sheath so as to prevent movement of the guide element relative to the sheath; (c) guiding the sheath and the guide element to the target location; (d) locking the sheath within the working channel to prevent relative movement of the sheath relative to the handle; and (e) unlocking and withdrawing the guide element from the sheath so as to leave the lumen of the sheath in place as a guide for inserting a tool to the target location.

There is also provided according to the teachings of the present invention, the guide element includes a position sensor element, the position sensor element being part of a position measuring system measuring a position and a pointing direction of a tip of the guide element relative to a three-dimensional frame of reference.

There is also provided according to the teachings of the present invention, a selectively actuatable anchoring mechanism is associated with a portion of the sheath.

There is also provided according to the teachings of the present invention, the selectively actuatable anchoring mechanism includes an inflatable element.

There is also provided according to the teachings of the present invention, the selectively actuatable anchoring mechanism includes a mechanically deployed element.

There is also provided according to the teachings of the present invention, at least a distal part of the sheath is treated so as to be substantially radio-opaque.

There is also provided according to the teachings of the present invention, at least one radio-opaque marked is associated with a distal end of the sheath.

There is also provided according to the teachings of the present invention, the guide element further includes an image sensor deployed for generating an image in the pointing direction of the catheter, the image sensor being withdrawn from the sheath as part of the guide element.

There is also provided according to the teachings of the present invention, a field of view of the image sensor is illuminated by using at least a distal portion of the sheath as an optical waveguide.

There is also provided according to the teachings of the present invention, illumination is supplied to the optical waveguide from at least one light source mounted within the guide element.

There is also provided according to the teachings of the present invention, illumination is supplied to the optical waveguide from at least one light source associated with the handle.

There is also provided according to the teachings of the present invention, the guide element further includes a radioactivity sensor, the sensor being withdrawn from the sheath as part of the guide element.

There is also provided according to the teachings of the present invention, a steering mechanism for selectively deflecting a distal portion of a steerable catheter in any one of at least two independent directions, the mechanism comprising: (a) at least three elongated tensioning elements extending along the catheter and configured such that tension applied to any one of the tensioning elements causes deflection of a tip of the catheter in a corresponding predefined direction; (b) an actuator displaceable from a first position to a second position; and (c) a selector mechanism configured for selectively mechanically interconnecting a selected at least one of the elongated tensioning elements and the actuator such that displacement of the actuator from the first position to the second position applies tension to the selected at least one of the elongated tensioning elements.

According to a further feature of the present invention, a first state of the selector mechanism mechanically interconnects a single one of the elongated tensioning elements with the actuator such that displacement of the actuator generates deflection of the tip in one of the predefined directions, and a second state of the selector mechanism mechanically interconnects two of the elongated tensioning elements with the actuator such that displacement of the actuator generates deflection of the tip in an intermediate direction between two of the predefined directions.

According to a further feature of the present invention, the at least three tensioning elements includes an even number of the tensioning elements, pairs of the tensioning elements being implemented as a single elongated element extending from the selector mechanism along the catheter to the tip and back along the catheter to the selector mechanism.

According to a further feature of the present invention, the at least three tensioning elements is implemented as four tensioning elements deployed such that each tensioning element, when actuated alone, causes deflection of the tip in a different one of four predefined directions separated substantially by multiples of 90°.

According to a further feature of the present invention, a first state of the selector mechanism mechanically interconnects a single one of the elongated tensioning elements with the actuator such that displacement of the actuator generates deflection of the tip in one of the four predefined directions, and a second state of the selector mechanism mechanically interconnects two of the elongated tensioning elements with the actuator such that displacement of the actuator generates deflection of the tip in one of four intermediate directions each lying between two of the four predefined directions.

According to a further feature of the present invention, the actuator includes a ring which is slidable relative to a handle associated with the catheter, and wherein the selector mechanism includes a slide attached to each of the tensioning elements and slidably deployed within the handle and at least one projection projecting from the ring such that, when the ring is rotated, the at least one projection selectively engages at least one of the slides such that displacement of the ring causes movement of the at least one slide.

BRIEF DESCRIPTION OF THE DRAWINGS

The invention is herein described, by way of example only, with reference to the accompanying drawings, wherein:

FIGS. 18A, 18B and 18C are additional tip-to-target displays in sagittal, AP and axial representations, respectively;

DESCRIPTION OF THE PREFERRED EMBODIMENTS

The present invention provides endoscope structures and corresponding techniques for navigating to a target in branched structure, such as the human lungs, and for bringing a medical tool to the target.

The principles and operation of endoscopes and navigation techniques according to the present invention may be better understood with reference to the drawings and the accompanying description.

Before addressing the drawings directly, it will be helpful to understand that the present invention provides a system and corresponding methods including multiple features each of which is believed to be patentable in its own right, and many of which may have utility independent of the other features of the invention in contexts other than the context described herein. For clarity of presentation, as well as to illustrate the synergy between the different aspects of the invention when combined, the various features will be described herein in the context of a combined system and accompanying procedural techniques with only a small number of variants described explicitly. The applicability of the various features of apparatus and methods according to the present invention, and as defined by the appended claims, in other contexts will be self explanatory to one ordinarily skilled in the art.

By way of general introduction, one primary aspect of the present invention, common to many of the aforementioned patentable features, is a structure and method which addresses the limitations of the conventional bronchoscope as discussed above by providing a small gauge steerable catheter including a locatable guide within a sheath. The outline of a typical procedure using this catheter is as follows:

a. The location of a target in a reference coordinate system is detected or imported.

b. The catheter is navigated to the target while tracking the distal tip of the guide in the reference coordinate system. Insertion of the catheter is typically via a working channel of a conventional bronchoscope.

c. Once the tip of the catheter is positioned at the target, the guide is withdrawn, leaving the sheath secured in place.

d. The sheath is then used as a guide channel to direct a medical tool to the target.

For clarity of presentation, the following description will be subdivided as follows. First, with reference to FIGS. 1-7, the preferred structure of a catheter and the accompanying system constructed and operative according to the teachings of the present invention will be described. Then, with reference to FIGS. 8-16, various techniques for acquiring target locations within the reference coordinate system will be discussed. With reference to FIGS. 17A-21, various navigation aids, navigation techniques and associated corrections will be described. Finally, with reference to FIGS. 22 and 23, various aspects of the present invention relating to the use of medical tools inserted via a sheath will be discussed.

General Structure

Figure 1:
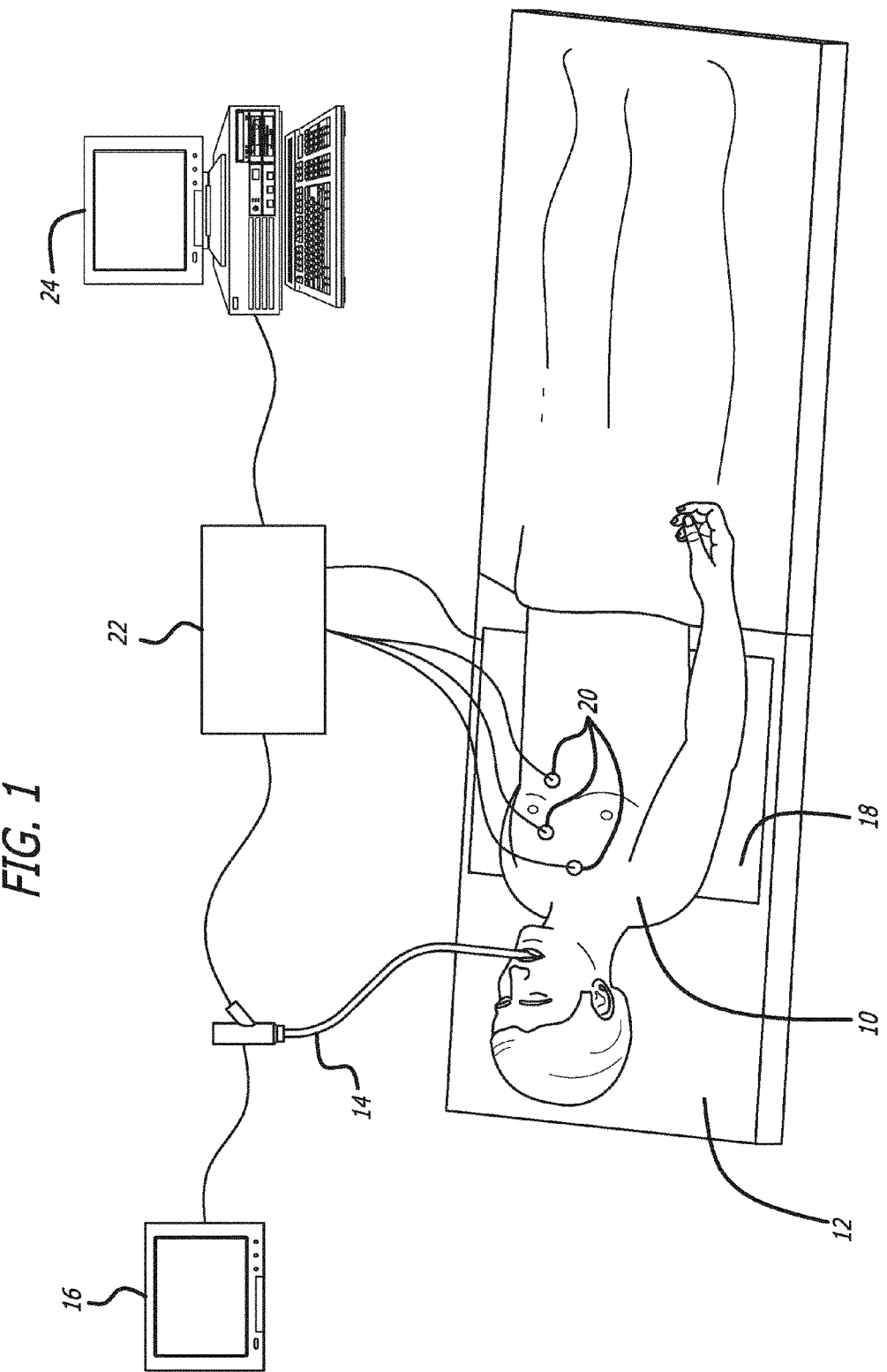
FIG. 1 is a schematic overall representation of a system, constructed and operative according to the teachings of the present invention, for navigating to a target within a branched structure.

Referring now to the drawings, FIG. 1 is a schematic overall representation of a system, constructed and operative according to the teachings of the present invention, for navigating to a target within a branched structure;

Specifically, FIG. 1 shows a patient 10 lying on an operating table 12. A bronchoscope 14 is inserted into his lungs. Bronchoscope 14 is connected to the monitoring equipment 16, and typically includes a source of illumination and an video imaging system. In certain cases, the device of the present invention may be used without a bronchoscope, as will be described below. A position measuring system monitors the position of the patient 10, thereby defining a set of reference coordinates. A particularly preferred position measuring system is a six degrees-of-freedom electromagnetic position measuring system according to the teachings of U.S. Pat. No. 6,188,355 and published PCT Application Nos. WO 00/10456 and WO 01/67035. In this case, a transmitter arrangement 18 is implemented as a matt positioned beneath patient 10. A number of miniature sensors 20 are interconnected with a tracking module 22 which derives the location of each sensor 20 in 6 DOF (degrees of freedom). At least one, and preferably three, reference sensors 20 are attached to the chest of patient 10 and their 6 DOF coordinates sent to a computer 24 where they are used to calculate the patient coordinate frame of reference.

Also visible in FIG. 1 is a catheter assembly 30, constructed and operative according to the teachings of the present invention, which is shown inserted via a working channel of bronchoscope 14. Catheter assembly 30 is shown more clearly in FIG. 2. Catheter assembly 30 includes a locatable guide 32 which has a steerable distal tip 34, a flexible body 36 and, at its proximal end, a control handle 38. Guide 32 is inserted into a sheath 40 within which it is locked in position by a locking mechanism 42. A position sensor element 44, operating as part of the position measuring system of FIG. 1, is integrated with distal tip 34 and allows monitoring of the tip position and orientation (6 DOF) relative to the reference coordinate system.

Turning now to the steering mechanism of catheter 30, it should be noted that the present invention may optionally be implemented with a conventional steering mechanism which provides a single direction of deflection. It has been found however that, due to the fine gauge of the catheter and extensive area in contact with surfaces of the surrounding lumen, it becomes difficult to reliably turn the catheter about its longitudinal axis to align the flexing direction with a desired steering deflection direction. To address this issue, the present invention preferably provides a multi-directional steering mechanism with a manual direction selector which allows selection of a steering direction by the practitioner without rotation of the catheter body. It should be noted that the steering mechanism described herein is useful in a wide range of applications independent of the other features of the present invention, and is believed to be patentable in its own right.

Figure 3:
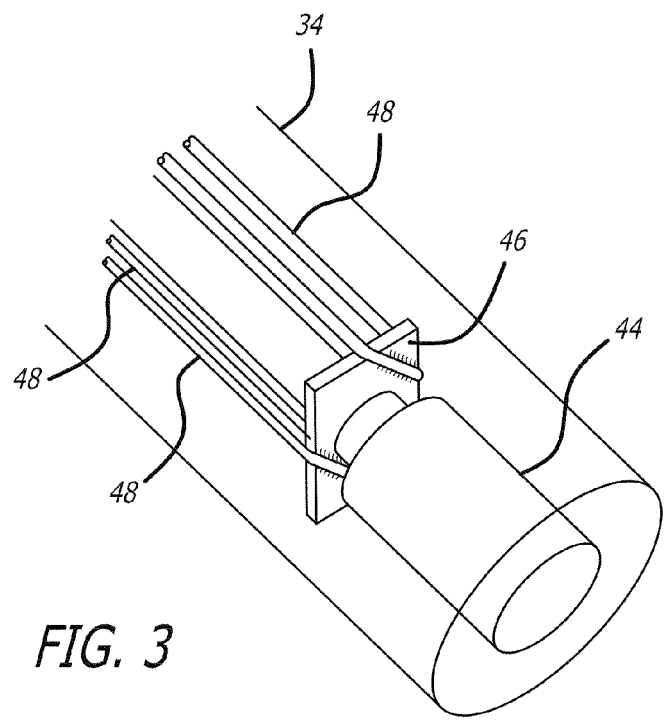
FIG. 3 is a schematic isometric view of a tip portion of the catheter of FIG. 2.
Figure 4A:
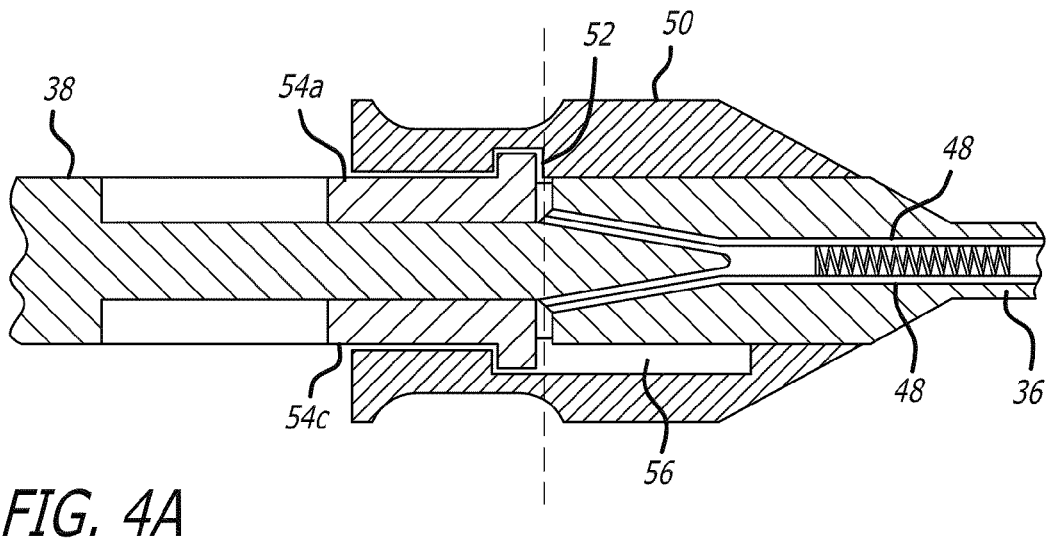
FIGS. 4A and 4B are schematic cross-sectional views through a steering mechanism controller from the catheter of FIG. 2 in a non-actuated state, and an actuated state, respectively.
Figure 4B:
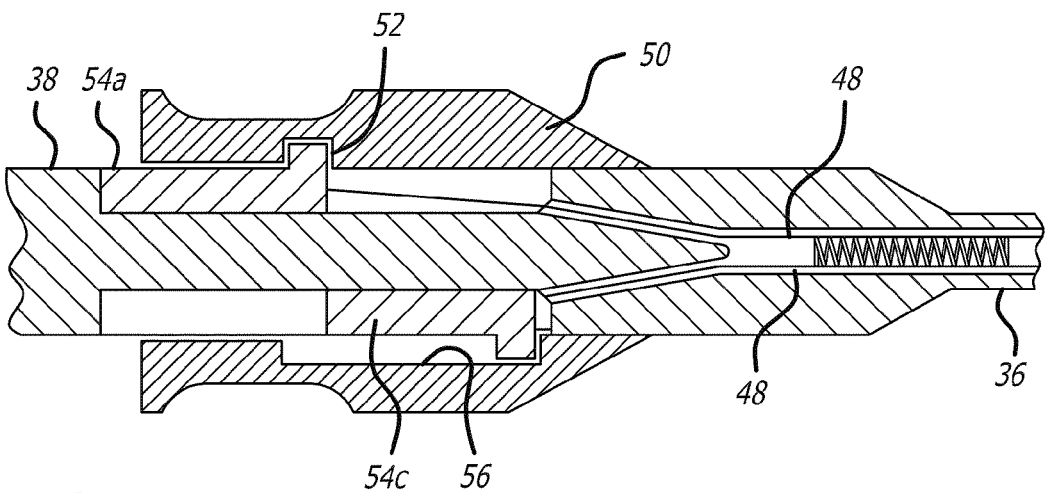

Turning now to FIG. 3, this shows an enlarged view of distal tip 34 with position sensor element 44 mounted on a base 46 to which at least three, and preferably four, elongated tensioning elements ("steering wires") 48 are attached. Steering wires 48 are deployed such that tension on each wire individually will steer the tip towards a predefined lateral direction. In the preferred case of four wires, the directions are chosen to be opposite directions along two perpendicular axes. In other words, the four wires are deployed such that each wire, when actuated alone, causes deflection of said tip in a different one of four predefined directions separated substantially by multiples of 90°. For practical reasons of ease of manufacture and reliability, wires 48 are preferably implemented as pairs of wires formed from a single long wire extending from handle 38 to tip 34, bent over part of base 46, and returning to handle 38, as shown.

Figure 2:
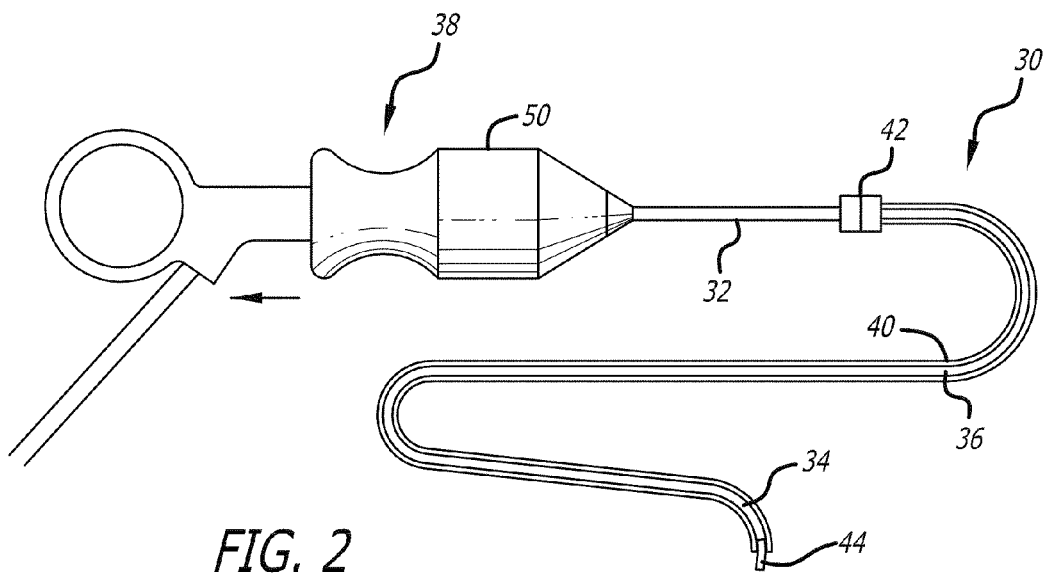
FIG. 2 is a schematic side view of a steerable catheter, constructed and operative according to the teachings of the present invention, for use in the system of FIG. 1.

Referring now back to FIG. 2, and to the cross-sectional views of FIGS. 4A-5C, handle 38 has an actuator, displaceable from a first position to a second position, and a selector mechanism for selectively mechanically interconnecting at least one of the steering wires and the actuator such that displacement of said actuator from its first position to its second position applies tension to a selected one or more of steering wires 48. In the implementation shown here, the actuator is implemented as a slidable collar 50 which can be drawn rearwards relative to a fixed portion of handle 38. The selector mechanism is here implemented as best seen in FIGS. 4A-5C as a rotational dial mechanism where a ridge, projection or step 52 on an internal surface of collar 50 selectively engages one or more slides, implemented here as actuator blocks 54a, 54b, 54c, 54d, each of which is connected to a steering wire 48. When collar 50 is slid from its initial position (FIG. 4A) to its retracted position (FIG. 4B), step 52 engages one or more actuator block (here block 54a) so as to apply tension to the corresponding wire 48. The remaining actuator blocks (only 54c is visible in FIG. 4B) remain in place.

Figure 5A:
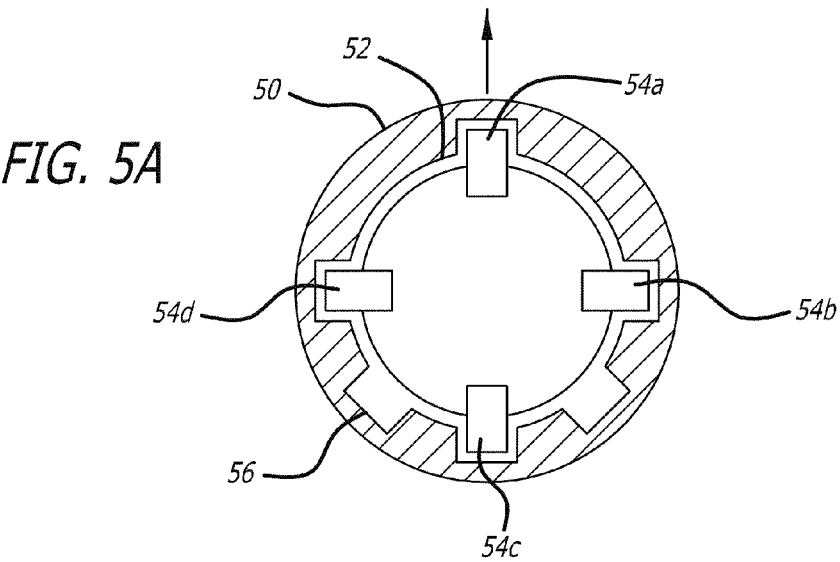
FIGS. 5A-5C are cross-sectional views taken along the line V-V in FIG. 4A showing a steering direction selector in first, second and third positions, respectively.
Figure 5B:
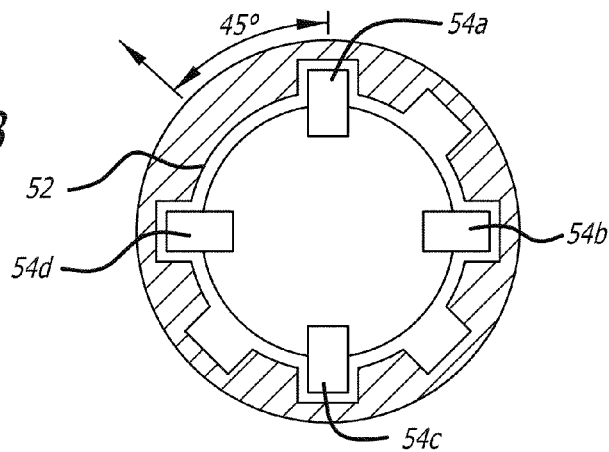
Figure 5C:
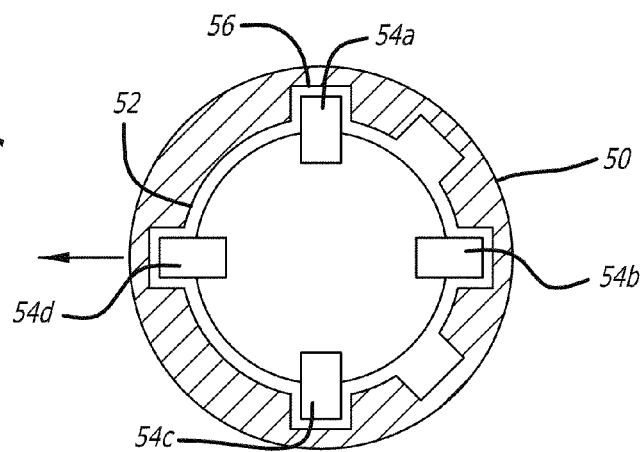

FIGS. 5A-5C show an axial view of the selector mechanism in three different states. In FIG. 5A, step 52 overlaps the actuator block 54a corresponding to the steering wire for upward deflection of the guide element. Clearance slots 56 ensure that the remaining actuator blocks 54b, 54c, 54d are not affected by sliding of collar 50. In FIG. 5B, collar 50 has been turned 45° such that step 52 overlaps two adjacent actuator blocks 54a and 54b. In this position, sliding of collar 50 applies tension to the corresponding two steering wires at the same time, thereby causing deflection of distal tip 34 in an intermediate direction between the predefined primary directions. FIG. 5C shows the selector mechanism after collar 50 has been turned through a further 45° such that it now engages exclusively the actuator block 54d on the left side of the figure as viewed.

It will be apparent that the structure described offers a highly controllable and easily operated steering mechanism in which a plurality of steering wires provides selective deflection of the catheter tip in any of at least two independent directions. "Independent directions" are hereby defined in this context as flexing directions which are non-coplanar. In the preferred example illustrated here, four steering wires provide eight different steering directions, selectable by the turn of a dial, spaced at roughly 45° increments. In a further variant implementation (not shown), the actuator and/or selector mechanism are configured to apply uneven tension on two wires so as to achieve additional intermediate steering directions or a substantially continuously adjustable steering direction. A simple implementation of such a mechanism employs a V-shaped actuator step such that mechanical engagement with the actuator blocks occurs an adjustable axial distance from the rest position of the actuator.

Clearly, the mechanical implementation of the actuator and selector mechanism may vary considerably. Minor variations include implementation of the selector mechanism as a separate ring mounted in collar 50, and implementation of step 52 as isolated inwardly-projecting engagement teeth rather than a near-continuous internal ridge. Other non-limiting examples of possible variants include different implementations of the actuator such as by a trigger-type mechanism.

Figure 6A:
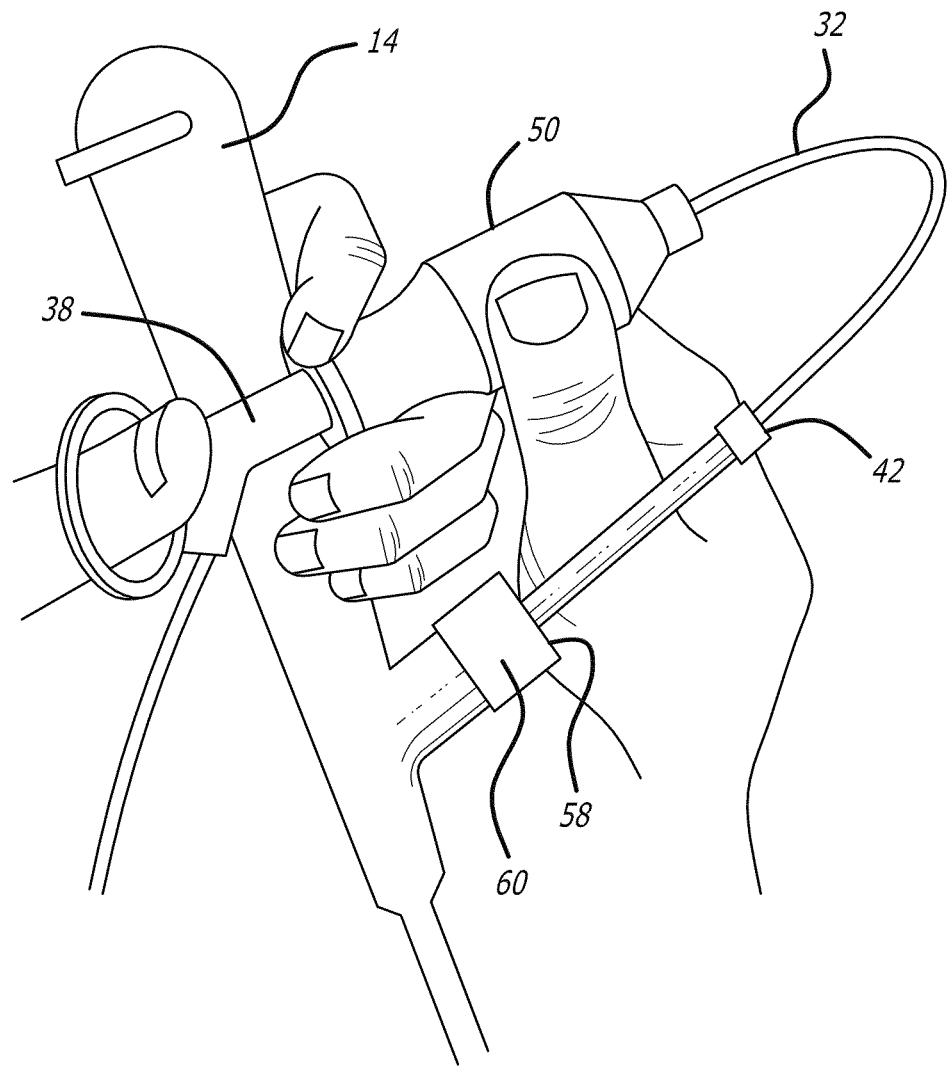
FIG. 6A is a schematic isometric view showing the hand position of a practitioner during selection of a steering direction of the catheter of FIG. 2.
Figure 6B:
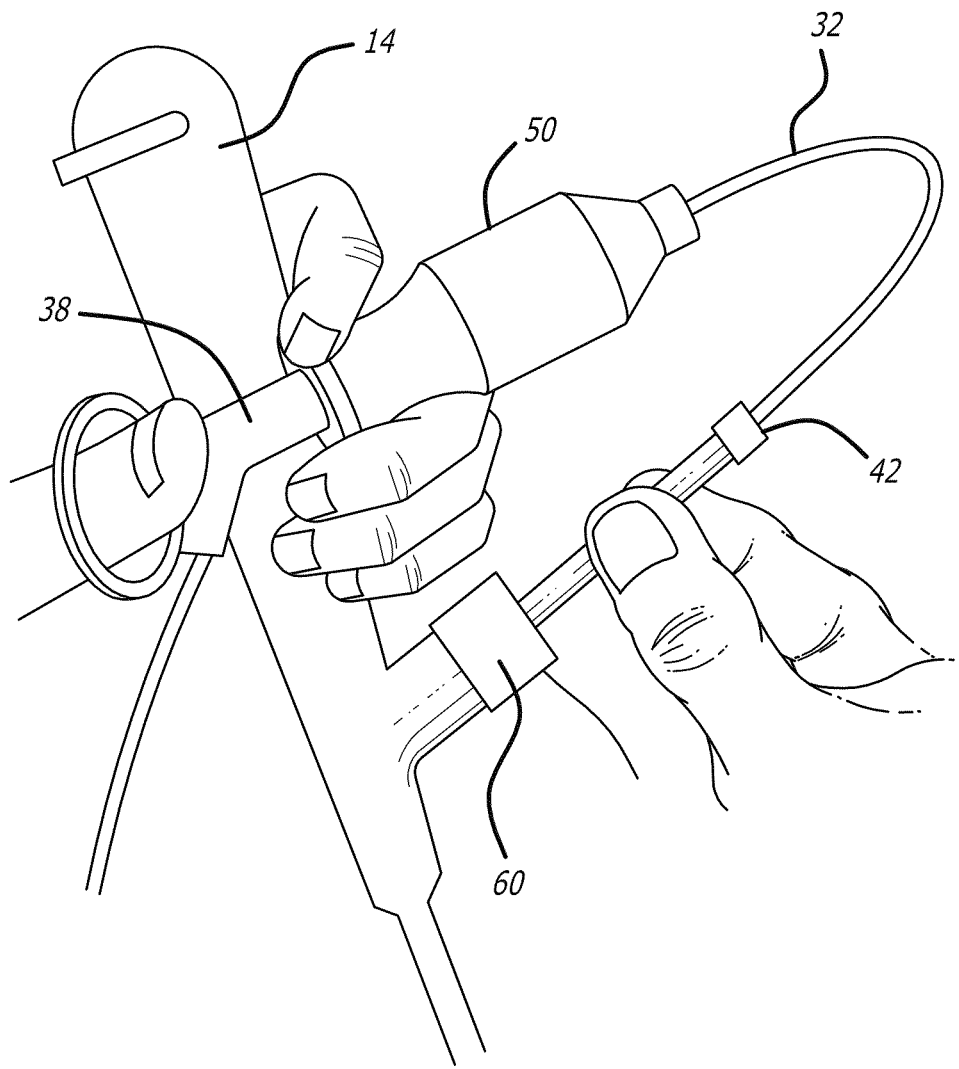
FIG. 6B is a schematic isometric view showing the hand position of a practitioner during navigation of the catheter of FIG. 2.

FIGS. 6A and 6B illustrate the ergonomic advantages of the preferred implementation of the steering mechanism control as described. After insertion of the distal tip (not shown) of the bronchoscope 14 as far as it can reach in the bronchial tree, catheter 30 is inserted into the bronchoscope's working channel via the working channel entrance 58. The external diameter of sheath 40 is preferably slightly less than the 2.8 mm diameter common in many bronchoscope working channels to facilitate insertion via a standard bronchoscope. The catheter is then advanced beyond the end of the bronchoscope towards the target. The handle 38 of locatable guide 32 is configured to allow the practitioner to hold it, and operate the steering mechanism actuator, with the same hand (typically the left hand) with which he is holding the bronchoscope. This leaves his or her right hand free. To steer the guide in a desired direction, collar 50 is rotated to select the direction in which the guide will be deflected (FIG. 6A). Then, while advancing the locatable guide into the working channel with the right hand, steering collar 50 is retracted by squeezing together the fingers on collar 50 towards the thumb located at the rear of handle 38, as shown in FIG. 6B. Once the tip of the guide reaches the target, a locking arrangement 60 is locked to stabilize sheath 40 relative to bronchoscope 14. Locking mechanism 42 is then unlocked to release guide 32 from sheath 40. The guide is then withdrawn from sheath 40, leaving the sheath free to accept any therapeutic tool, such as biopsy forceps.

Figure 7:
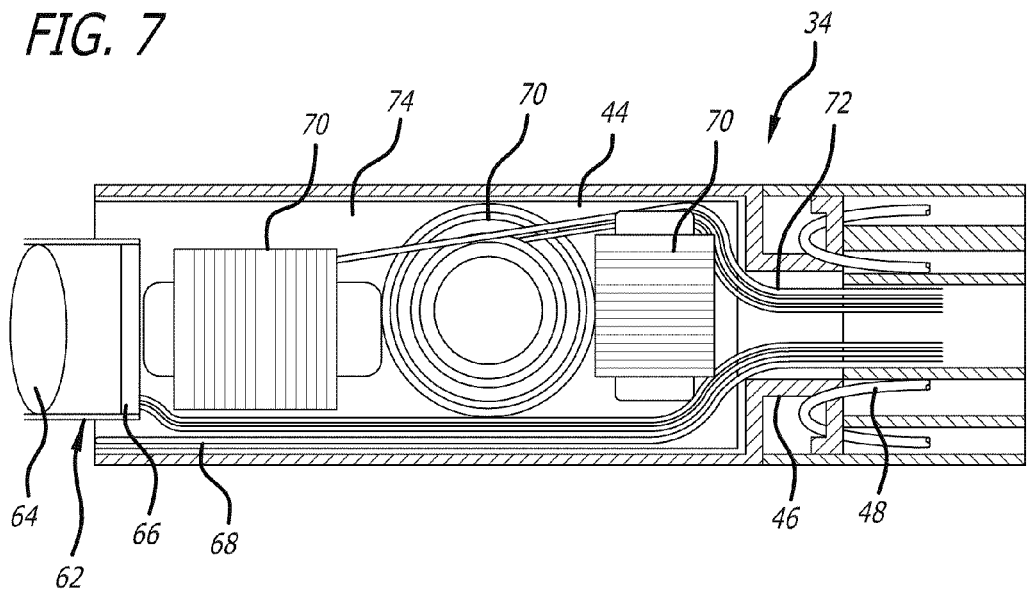
FIG. 7 is a schematic cross-sectional view of an alternative implementation of the tip portion of the catheter of FIG. 2 including an image sensor.

Turning now to FIG. 7, there is shown an alternative implementation of tip portion 34, generally similar to that of FIG. 3, but in this case including at least part of an imaging system, in this case an image sensor 62. Image sensor 62 is shown here in a preferred implementation as an optical imaging sensor with a lens 64 positioned in front of an image sensor array 66. Illumination is preferably provided via an optic fiber light guide 68.

Given the strict limitations on dimensions of the sensor (requiring a diameter less than 2 mm), it is preferably implemented using CMOS or CCD imaging sensor technology integrated with lens 64 by micro-production techniques. Most preferably, image sensor 62 is integrated into location sensor element 44. Specifically, the structure of the location sensor element according to the most preferred implementation of the invention includes a plurality of coils 70 and their connecting wires 72, typically fixed in a block of adhesive 74. In this case, image sensor 62 is preferably fixed in the same adhesive block. Optic fiber 68 may also be included in block 74, if lateral dimensions allow.

In some cases, production limitation and/or the lateral dimensions of the tip may not allow optic fiber 68 to extend through the sensor block. In this case, the preferred solution is to position optic fiber 68 with its end near the proximal side of block 74 which, at least in this case, is made of generally transparent, or at least somewhat translucent, material. In this case, sufficient light diffuses through the material of block 74 around and between the suspended components to provide illumination of the field of view of image sensor 62 beyond the distal end of the assembly. A further alternative for providing illumination is to use at least a distal portion of sheath 40 as an optical waveguide. The illumination in this case may also be delivered by optic fiber 68 terminating on the proximal side of block 74, by one or more light source mounted within guide element 32, or by a light source associated with handle 38 which delivers light directly to the proximal end of sheath 40.

In other respects, tip portion 34 is similar to that of FIG. 3, including doubled-over steering wires 48 attached to base 46. Seen more clearly here is a preferred subdivision of the flexible body 36 into five internal lumens: one for each of the four steering wires and a central lumen containing the electrical wires from the various sensors and the optic fiber for illumination.

It will be clear that the addition of an image sensor to tip portion 34 provides enhanced functionality as a small-gauge bronchoscope. As will be discussed below, this configuration may be used to advantage without a conventional bronchoscope. Nevertheless, given the image sensor size requirements and the limitations of current technology, the image quality from sensor 62 will typically be significantly lower than that of a conventional bronchoscope. For this and other reasons, it is envisaged that image sensor 62 will be used primarily as an additional enhancement to a device for use in conjunction with a bronchoscope, further facilitating navigation of the catheter of the present invention beyond the range of the bronchoscope.

Target Acquisition Techniques

In order to employ the location measurement system of the present invention as a navigational aid, it is necessary to identify one or more target location in the reference coordinate system. This may be done directly, or by importing location data from an offline source, such as computerized tomography (CT) data. Direct acquisition requires an imaging device or other detector which can be used non-invasively to locate the target. Importing targets from offline data requires registration of the offline data with the reference coordinate system. Various examples of both groups of techniques will now be described.

Isotopic Triangulation

Figure 8:
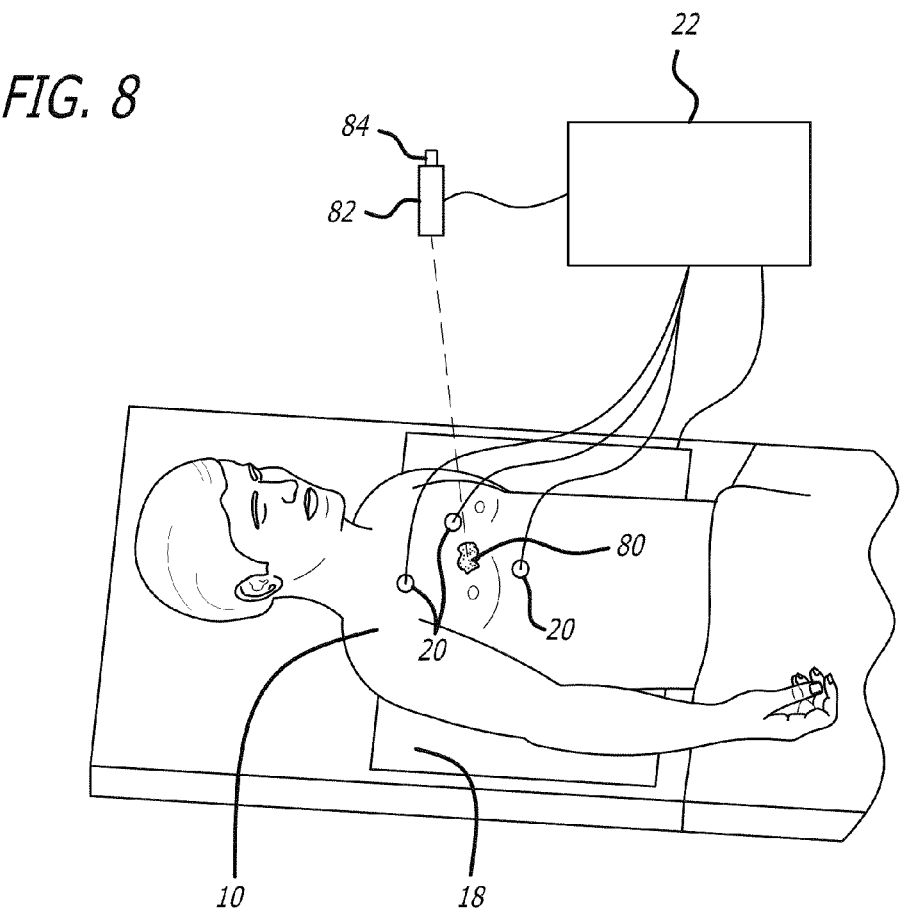
FIG. 8 is a schematic isometric view illustrating an arrangement for acquiring a target location in a position sensor frame of reference using isotopic labeling and an external detector.

FIG. 8 illustrates an arrangement for acquiring a target location in a position sensor frame of reference using isotopic labeling and an external detector. According to this technique, a shot of isotope solution is injected into the patient. The isotope is preferably the same as those used in PET protocols. It is known in the art that, after the solution is absorbed by the body, its concentration in a lesion is higher than in other parts of the body, thereby "marking" the lesion by elevated emission levels. In the case illustrated here, a lesion 80 within the chest of patient 10 has been thus marked by injection of a radioactive isotope. A detector 82 coupled with a 6 DOF location sensor element 84 is directed to sense this emission. Detector 82 is chosen to have a directional sensitivity profile which allows identification of a direction towards a source of highest emission. In a simple case, this is merely a detector with a direction of highest sensitivity, defined as the "axis" of the detector, which is adjusted until it gives a maximum reading. Alternatively, given a sensitivity profile of the detector and readings taken in a few different directions, a direction towards the source of maximum emission may be derived mathematically. The multiple readings may optionally be obtained simultaneously by a detector head with multiple sensors. At each stage, the position and pointing direction of the detector in the reference coordinate system is derived by tracking system 22 based on outputs of location sensor element 84.

Figure 9:
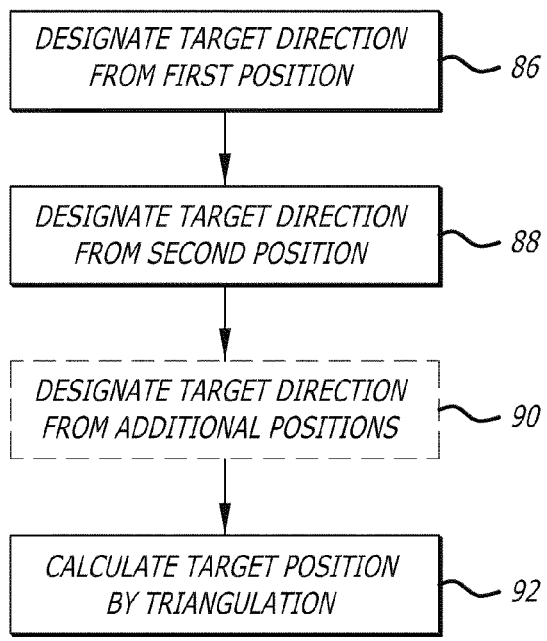
FIG. 9 is a block diagram illustrating a procedure for acquiring a target location using an external detector such as in the arrangement of FIG. 8.

FIG. 9 illustrates the procedure for acquiring a target location using an external detector such as in the arrangement of FIG. 8. First, at step 86, a direction to the target is determined from a first point of view. It will be appreciated that the combination of a direction towards the target (in this case, the direction to the source of maximum emission) and the position of the detector together define a line in space passing through the target. Then, at step 88, the detector is relocated to a new position and the direction to the target is again identified, thereby defining a second line in space passing through the target. Optionally, this procedure is repeated from one or more additional detector positions (step 90). The intersection (or point of closest proximity) of all of these lines is then derived (step 92), thereby defining the position of the target in the reference coordinate system.

Fluoroscopic Triangulation

A similar technique can be used without isotropic labeling by use of fluoroscopic imaging. Specifically, by replacing the detector 82 of FIG. 8 which a fluoroscope system, it is possible to identify the target within the image and designate the direction to the target. Here too, target direction designation may be achieved most simply by aligning the fluoroscope with a physical axis, typically indicated by crosshairs in the display, aligned with the target. In all other respects, the technique proceeds exactly as described in FIG. 9 by defining the direction to the target from two or more positions and identifying the intersection of the resulting lines as the target position.

Manual CT Registration

Although the isotopic labeling and fluoroscope-based solutions described above provide important solutions for cases where CT data is not available, it is generally believed to be highly preferable to integrate the system of the present invention with CT data.

By way of introduction, the use of CT as a diagnostic tool has now become routine and CT results are now frequently the primary source of information available to the practitioner regarding the size and location of a lesion. This information is used by the practitioner in planning an operative procedure such as a biopsy, but is only available as "offline" information which must typically be memorized to the best of the practitioner's ability prior to beginning a procedure. As will be discussed below, in addition to inputting target information, integration with the CT data provides important additional system functionality, thereby greatly facilitating navigation to the target location.

In contrast to the two prior methods, the CT data has its own system of coordinates. Matching the two system of coordinates, that of the CT and that of the patient, is commonly known as registration. Registration is generally performed by identifying at least three locations in both the CT and on or inside the body, and measuring their coordinates in both systems.

Figure 10:
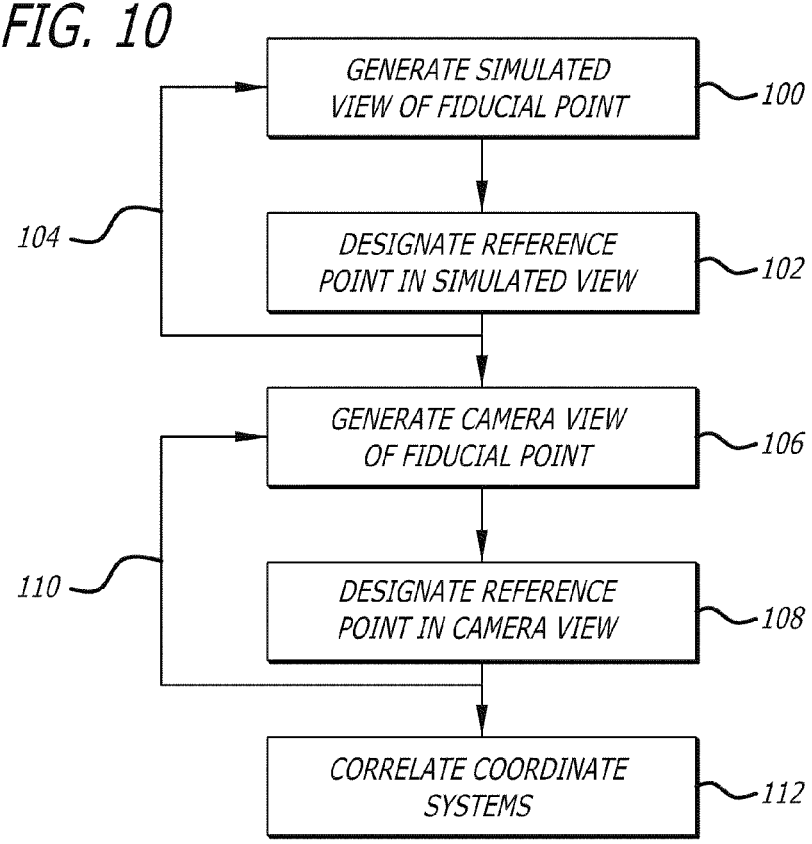
FIG. 10 is a block diagram illustrating a first procedure according to the present invention for correlating CT data with a location measurement system.
Figure 11:
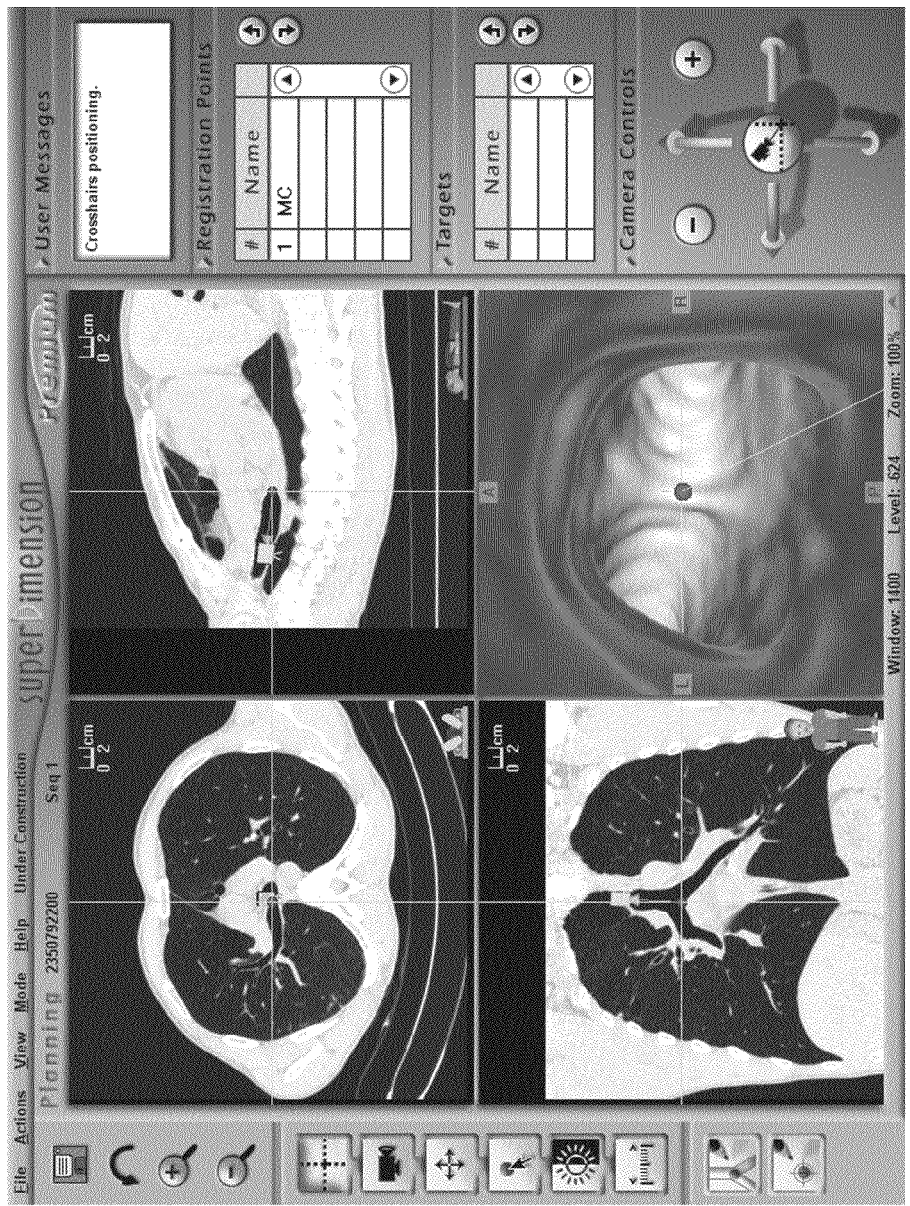
FIG. 11 is a display screen from a CT-based virtual bronchoscopy system including a simulated view of the carina between the main left and right bronchi for designation of a fiducial point for the procedure of FIG. 10.

Turning now to FIGS. 10-12, a first procedure according to the present invention for correlating CT data with a location measurement system will be described. Generally speaking, the technique as illustrated in FIG. 10 starts by generating from the CT data a simulated view of a distinctive feature within the branched structure (step 100) and designating a reference point viewed within the simulated view (step 102). This is repeated (arrow 104) until at least three, and preferably 5-10 CT reference points have been designated. Then, during performance of a procedure on the patient, the bronchoscope or other image sensor is positioned to view one of the same group of distinctive features (step 106) so that the camera view corresponds to, and is generally similar to, a corresponding one of the simulated views. The operator then designates a reference point viewed within the camera view equivalent to the corresponding reference point designated in the corresponding simulated view (step 108), such as by contacting the point with the position sensor element. Steps 106 and 108 are repeated (arrow 110) until three or more pairs of corresponding reference points are obtained. The designated reference points are then used to derive a best fit registration between the computerized tomography image and the three-dimensional frame of reference (step 112).

Figure 12A:
FIG. 12A is a bronchoscope view of the carina similar to the simulated view of FIG. 11.
Figure 12B:
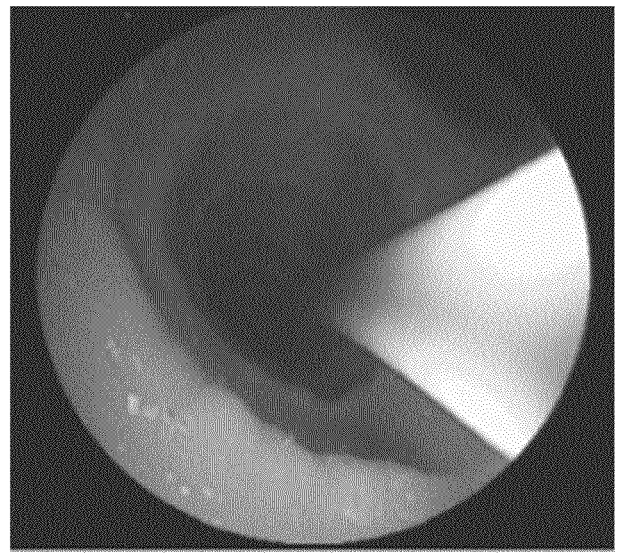
FIG. 12B is a view similar to FIG. 12A after the bronchoscope has been advanced to bring a location sensor into proximity with a point on the carina for use as a fiducial point in the procedure of FIG. 10.

The implementation of this technique will be better understood from FIGS. 11-12B. Prior to beginning the procedure, the volumetric CT data is stored and transferred to computer 24 or another suitably programmed medical imaging workstation, either using the hospital Ethernet or from a data storage medium such as a compact disk (CD). The practitioner then needs to designate the required reference points. Preferably, the reference points used are easily identified anatomical landmarks, referred to a "fiducial points". In principle, the fiducial points could be selected in a conventional two-dimensional "slice" display of the CT data. In practice, however, this does not result in sufficiently accurate registration, as will now be explained.

The accuracy of the registration is dependent upon the ability to precisely define and mark the reference points. In the bronchial tree, the available anatomical landmarks are the bifurcations of the bronchi which are up to a few centimeters in size for those at the entry of the bronchus. If these junctions are used as fiducial "points" or regions, the result would typically be very imprecise registration, unless very many such points are taken. On the other hand, if the practitioner is required to match too many points, the entire procedure becomes inefficient. Accordingly, the present invention provides a technique for enhancing the ability of a practitioner to select equivalent points within the region of the bifurcation at a much higher resolution than the overall dimensions of the bifurcation. Specifically, this is done by using CT-based "virtual bronchoscopy" to generate simulated views similar to the actual bronchoscope views. Virtual bronchoscopy is a computer simulation technique in which CT data is used to construct a virtual model of airways within the body tissue, and this model is used to generate simulated views similar to those viewed by a bronchoscope. The technology of virtual bronchoscopy is described in U.S. Pat. Nos. 6,246,784 and 6,345,112 both to Summers et al., as well as the references cited therein, all of which are hereby incorporated herein by reference. In this context, the use of virtual bronchoscopy allows the practitioner to employ his visual judgment based on factors such as symmetry and shape to designate equivalent reference points in both the CT data and the reference coordinate system with much greater precision than would otherwise be possible.

Turning now to FIG. 11, this shows a display screen from a preferred implementation of a planning program which generates virtual bronchoscopy registration images for use in the present invention. The display as shown is divided primarily into four views. Three of these views display mutually perpendicular two-dimensional "slice" views derived from the CT data. The upper left view is an axial projection of the patient. The right upper view is a sagittal projection. The lower left view is an anterior-posterior ("AP") view. In each view, a crosshair indicates the planes of the other two slices currently displayed, all three planes intersecting at a point in the CT coordinate frame. In the lower right region, a virtual image of the bronchus at the selected point is displayed. In this case, the selected point is on the carina, the upper junction of the bronchial tree. The software also allows adjustment of the viewing direction which, for this procedure, is chosen to be the direction from which a real bronchoscope will approach the region.

As can be seen, the carina junction is long and does not in itself define any single point. Nevertheless, by taking into account the symmetry of the carina, a practitioner can designate a reference point at a middle location along the carina, where the septum is relatively narrow, in a repeatable manner with minimal error. This point is then marked as a selected fiducial point, and its coordinates in the CT coordinate frame are stored. This procedure is repeated until at least three, and preferably between 5 and 10, fiducial points have been recorded. This data is preferably then stored or transferred in a form in which it can be made available for visual display to the practitioner during the practical procedure.

Parenthetically, it will be noted that point selection in the simulated image is performed as selection of a point in the two-dimensional image on screen using a mouse or other computer input device. Designation of the point in the three-dimensional CT data coordinate system is achieved by extrapolating from the selected point in the simulated viewing direction until the line intersects the closest tissue surface (according to the aforementioned numerical model of a portion of the body derived from the CT data).

During performance of the practical procedure, the first stored image is presented to the practitioner who guides the bronchoscope to the corresponding landmark feature within the patient. As the bronchoscope tip approaches the site, the bronchoscope views an image (FIG. 12A) very similar to the virtual image shown in the lower right panel of FIG. 11. The practitioner then designates the reference point, preferably by advancing location sensor 44 located at the tip of locatable guide 32 to touch a point equivalent to the location marked in the virtual image (FIG. 12B) and designating the sensor position as the corresponding fiducial point in three dimensions in the reference coordinate system. This is repeated for a total of at least three, and preferably for all 5-10, fiducial points designated in the virtual bronchoscopy stage. On the basis of the accumulated data, a best fit mapping (typically, translation and rotation) between the CT fiducial points and the reference coordinate system is derived. The possibility of a more complex distortion-correcting mapping will be discussed below with reference to FIG. 21.

Once a best fit mapping is derived, any and all information from the CT data becomes readily available for importing into the location measurement system frame of reference. Minimally, the location and possibly also the shape of the lesion is incorporated as target information by navigation software running on computer 24. Optionally, the data can also be used for importing a pre-planned route map to the target or to provide real-time CT and/or virtual bronchoscopy displays corresponding to the current location sensor position, as will be discussed further below.

Semi-Automated CT Registration

While the manual fiducial point designation of the above registration technique is highly effective, the choice of number of points sampled necessarily represents a tradeoff between accuracy and efficiency. In order to circumvent this tradeoff and speed up the procedure, an alternative semi-automated registration technique allows collection of a large number of sample points automatically within a very short time period. This technique will now be described with reference to FIGS. 13-16.

In general terms, this technique is based upon automated collection of multiple reference points on the interior surface of an airway followed by fitting of a geometrical model (typically a cylinder) to these points. Registration is then achieved by correlating this geometrical model to the corresponding feature(s) in a model based on the CT data.

Collection of the multiple reference point positions could be performed by moving position sensor 44 over regions of the surface directly. More preferably, the present invention provides a technique based on image processing which allows collection of reference point positions simply by advancing an image sensor associated with the position sensor along the airway.

Figure 13:
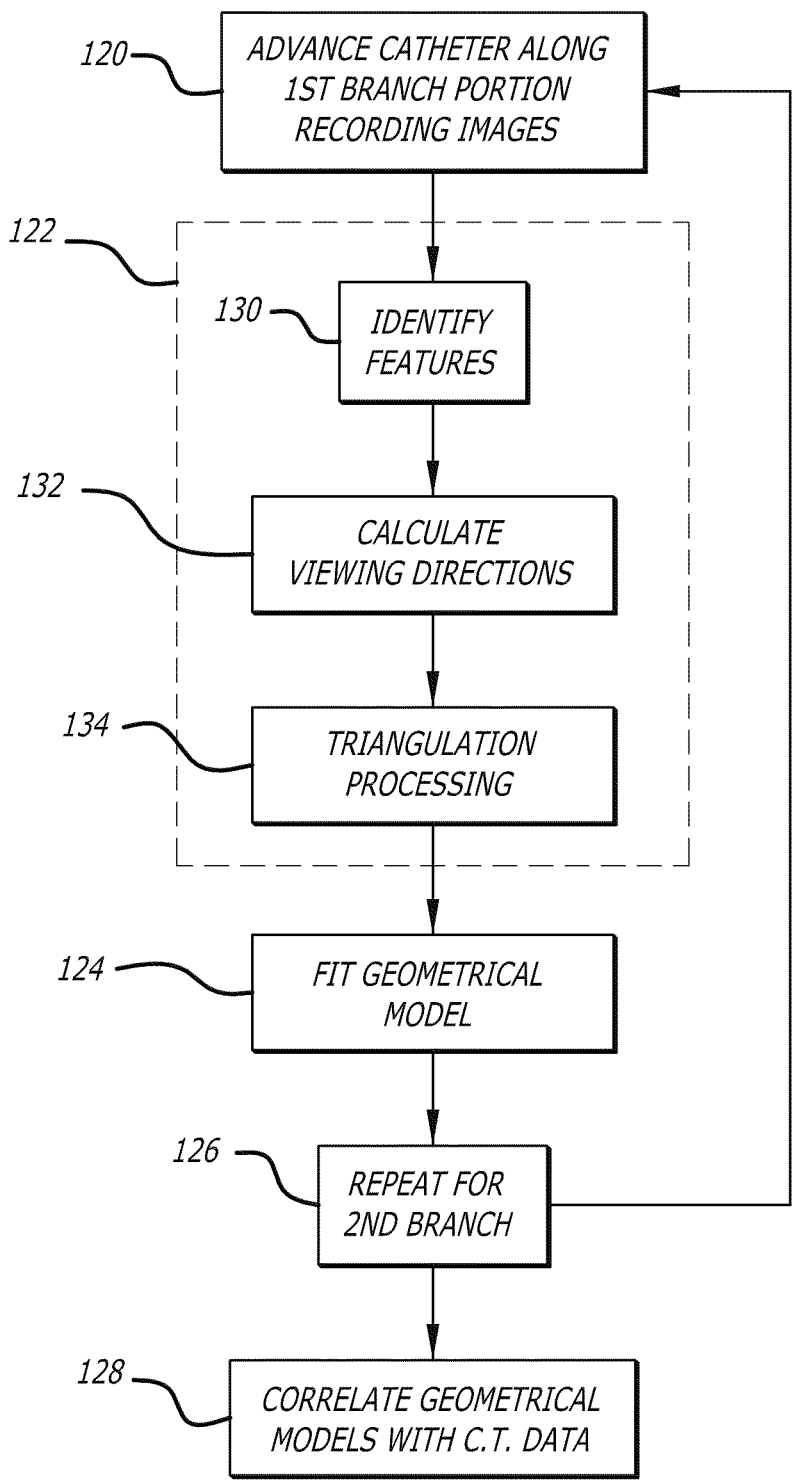
FIG. 13 is a block diagram illustrating a second procedure according to the present invention for correlating CT data with a location measurement system.

Turning now to FIG. 13, this shows steps of a preferred method according to the teachings of the present invention for achieving registration between computerized tomography data and a three dimensional frame of reference of a position measuring system. The method begins by moving the tip of the catheter along a first branch portion of the branched structure and deriving a plurality of images from the image sensor (step 120). Each image is associated with corresponding position data of the position sensor.

It will be noted that the image sensor may be either a conventional bronchoscope imaging system, or an image sensor built in to the catheter 30 of the present invention, such as is shown in FIG. 7. In either case, the spatial relation of the image sensor, including any lateral offset, must be determined before the procedure.

The images are then processed to derive position data for reference points on the surfaces of the tissue (step 122) and this position data is used to derive a best-fit of a predefined geometrical model to the first branch portion (step 124). Steps 120, 122 and 124 are then repeated for a second branch portion of the branched structure (step 126). Alternatively, the geometrical model may be a combined model for both branches in which case steps 120 and 122 are repeated first, and step 124 is performed once for the amassed data. The geometrical model(s) are then correlated with the CT data to derive a best fit registration between the computerized tomography data and the three dimensional frame of reference of the position measurement system (step 128). In the simple case of two non-parallel branch portions each modeled as a cylinder, the two resulting cylinders are sufficient to uniquely define a best fit mapping (translation and rotation) between the CT and position sensor coordinate systems.

In a preferred implementation, step 122 is performed as follows. Images taken from different positions along each branch are correlated to identify visible features which are present in plural images (step 130). These features may be any permanent or temporary visible features, including small blood vessels, localized variations in surface shape or color, and dust or other particles. For each of these features, a camera-to-feature direction is derived for each image showing that feature (step 132). These camera-to-feature directions and corresponding position sensor data are then used to determine a feature position for each visible feature (step 134).

Figure 14A:
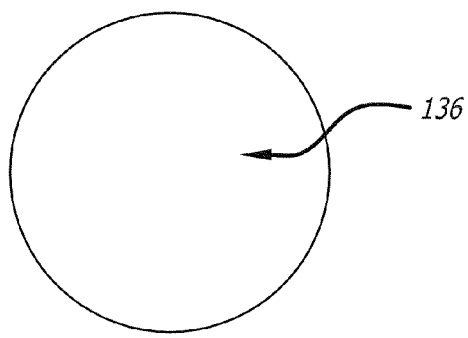
FIGS. 14A and 14B are schematic representations of views from an image sensor, such as that of the catheter of FIG. 7, showing an identifiable feature on the wall of a vessel as viewed from two viewing positions.
Figure 15A:
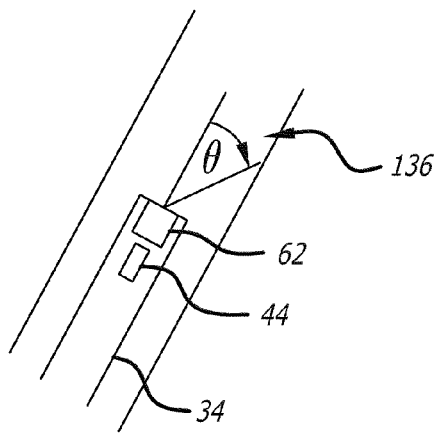
FIGS. 15A and 15B are schematic side views of the viewing positions of the tip of the catheter within part of a branched structure from which the views of FIGS. 14A and 14B, respectively, are obtained.
Figure 14B:
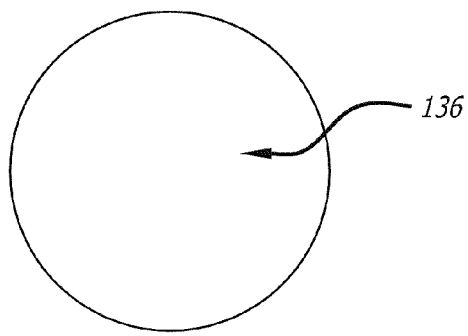
Figure 15B:
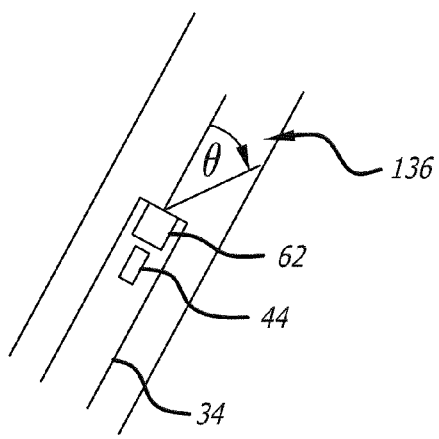
Figure 16:
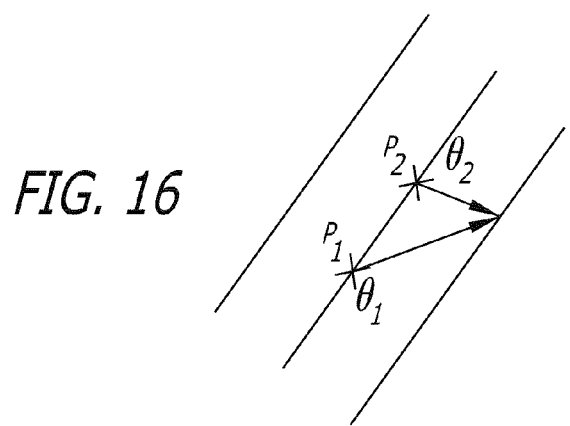
FIG. 16 is a schematic side view of the part of the branched structure indicating the determination of a location of the identifiable feature by triangulation.

This process is illustrated graphically in FIGS. 14A-16. FIGS. 14A and 14B illustrate schematically camera views taken from two different positions, a feature 136 being visible in both views. FIGS. 15A and 15B represent the corresponding positions of catheter tip 34 (with image sensor 62 and location sensor 44) from which these views were taken. It will be noted that the position of a feature in the camera view maps to a unique direction from the camera to the feature. Thus, by predetermining the optical characteristics of the camera (either by design, or by a calibration procedure such as by using a hemispherical dome with lights), the feature position in the image can be converted to a direction vector. In FIGS. 15A and 15B, this is illustrated schematically as off-axis angle ($\theta_1$, $\theta_2$). The real data also includes a second angle (rotation angle about the axis) together defining a unique camera-to-feature direction. By combining this information with the 6 DOF position sensor data (and any offset adjustment) from two positions, the feature position in three-dimensional space can readily be derived by simple triangulation, as shown in FIG. 16. Where data from more than two positions is available, it can be used to further improve accuracy.

Although illustrated here schematically for a single isolated feature, it is typically possible to derive tens, or even hundreds, of such feature positions from a length of airway. This allows an enhanced level of precision in the correlation procedure.

As before, once a best fit mapping is derived, any and all information from the CT data becomes readily available for importing into the location measurement system frame of reference. Minimally, the location and possibly also the shape of the lesion is incorporated as target information by navigation software running on computer 24. Optionally, the data can also be used for importing a pre-planned route map to the target or to provide real-time CT and/or virtual bronchoscopy displays corresponding to the current location sensor position, as will be discussed further below.

Navigation Techniques
Tip-to-Target Displays

Once a target location has been identified in the reference coordinate system, by one of the above techniques or otherwise, the device of the present invention is ready to assist in navigation to the target. The small air paths in the periphery of the lung are generally not detectable by the currently available real-time imaging devices. According to certain aspects of the present invention, the system provides tip-to-target displays and various other navigation aids to facilitate navigation to the target beyond the reach of the imaging system of a conventional bronchoscope.

Thus, according to a preferred method according to the present invention for steering a catheter through a branched structure to a target location, a representation is displayed of at least one parameter defined by a geometrical relation between the pointing direction of the tip of the catheter and a direction from the tip of the catheter towards the target location, while the catheter is moved within the branched structure. The at least one parameter preferably includes one or more of the following parameters: an angular deviation between the pointing direction of the tip of the catheter and a direction from the tip of the catheter towards the target location; a direction of deflection required to bring the pointing direction of the catheter into alignment with the target location; and a distance from the tip of the catheter to the target. It should be noted that each of the aforementioned parameters is a useful navigation aid in its own right. The angular deviation, even if appearing just as a numerical angle without any display of direction, can be used by trial and error to find a steering direction which reduces the deviation. Similarly, the direction of deflection can be used as a steering aid, even without a direct indication of the angular deviation. The distance to the target is also an important indicator of increasing proximity to the target. In a most preferred implementation, both the angular deviation and the direction of deflection are displayed, typically also with an indication of the distance to the target.

Figure 17A:
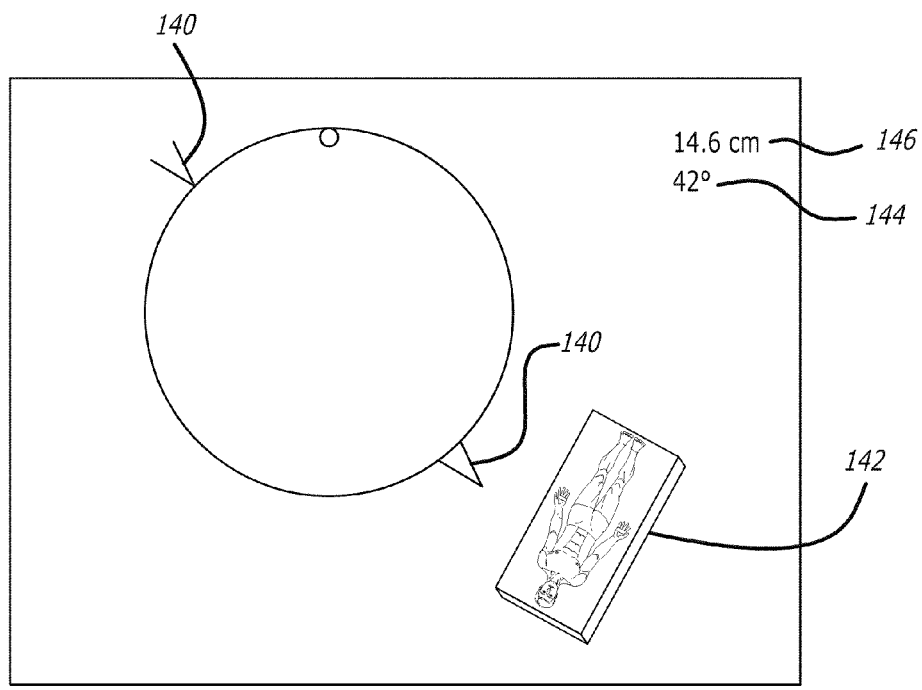
FIGS. 17A and 17B are schematic illustrations of a tip-to-target display at two stages during navigation of the catheter of FIG. 2 or FIG. 7 towards a target.
Figure 17B:
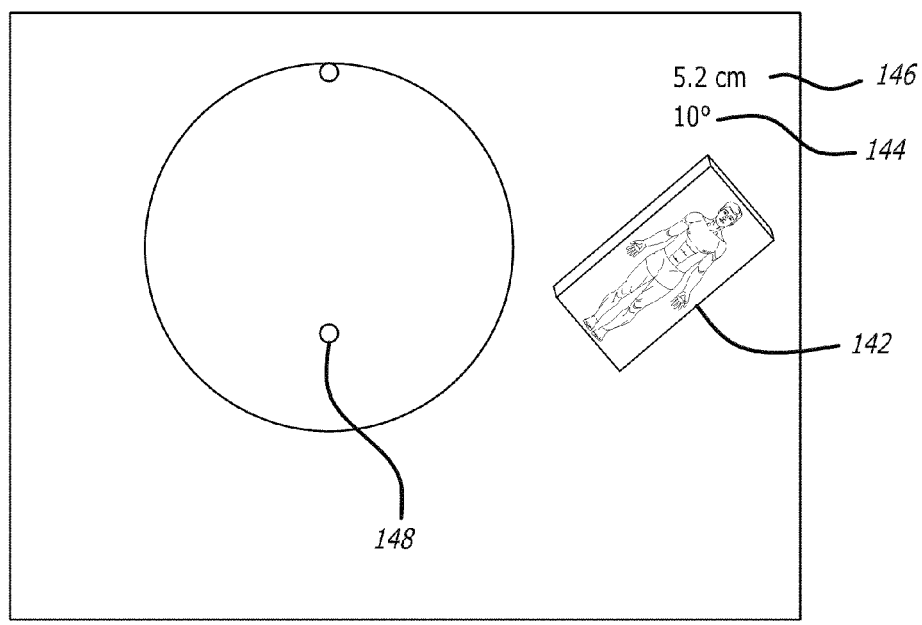

One particularly preferred display format is illustrated in FIGS. 17A and 17B which shows at least one of the parameters in the context of a representation of a view taken along the pointing direction of the tip of the catheter. This representation does not require any imaging system, being generated numerically from the 6 DOF location information for the catheter tip, the patient's body, and the target location.

The display as illustrated has three zones. The first is a circular display analogous to the straight-ahead viewing direction of a bronchoscope imaging system, but instead displaying graphically information regarding the direction to the target. In the case of FIG. 17A, the target is outside the forward-region defined by the circle. In this case, the required deflection direction to point towards the target is indicated by arrows 140. The orientation of the display is taken with the "up" steering direction of the catheter at the top of the display so that the practitioner can relate the display to the steering mechanism controls. The lower-right region of the display shows a pictogram 142 which illustrates graphically the relation of the "up" steering direction to the patient's body. Thus in the example of FIG. 17A, the catheter tip is currently pointing downwards towards the patient's back-left side with the "up" direction turning towards his chest. The third zone is an alphanumeric display which provides numerical data such as the angular deviation 144 to the target and the distance 146 to the target.

FIG. 17B shows the display after further advance of the catheter. In this case, the angular deviation is already sufficiently small that the target, as represented by symbol 148 appears within the circular display. In this case, pictogram 142 indicates that the "up" steering direction is actually currently towards the patient's back, i.e., down relative to the patient lying on the operating table.

Figure 19:
FIG. 19 is a display screen which combines the tip-to-target display of FIG. 17A with dynamic CT-based displays corresponding to axial, sagittal and AP planes passing through the current catheter tip position.

Preferably, the pointing direction display of FIGS. 17A and 17B is supplemented with various additional displays which facilitate interpretation by the practitioner during use, and provide various additional information or functionality to the practitioner. By way of example, FIGS. 18A-18C show computer graphic representations of the catheter tip 150 and target 148 in sagittal, AP and axial projections, respectively. (The additional lines appearing in these figures will be discussed below.) FIG. 19 shows a further example in which the tip-to-target display of FIG. 17A is combined with dynamic CT-based displays corresponding to axial, sagittal and AP planes passing through the current catheter tip position. A further preferred option (not shown) replaces or supplements the "slice" CT displays with a virtual bronchoscopy image corresponding to the current position and pointing direction of the catheter tip, thereby offering simulated functionality of a small gauge imaging catheter. In the case that catheter 30 is implemented with an image sensor 62 as in FIG. 7, the real image from the sensor is preferably provided.

Route Planning

Optionally, the CT or virtual bronchoscopy information can be used to pre-select a planned route to the target. Specifically, a series of locations may be selected on the CT slices, for example by use of a computer mouse. Each location is actually a coordinate in 3D space (two coordinates within the image and the third coordinate from the location of the slice itself). By connecting these locations, it is possible to draw a path in 3D space. If each location is taken from adjacent portions of interconnected air pathways inside the bronchial tree traced backwards from a target position to the bronchus (the entrance of the bronchial tree), the resulting path corresponds to a "roadmap" of a planned route to the target. This route, or steering data based upon the route, is then displayed together with the target data during the procedure.

The feasibility of route planning of this type depends upon the position of the target and the resolution of the CT data available. In certain cases, the distance between adjacent slices in the CT data is such that the course of the very fine airways between adjacent slices cannot be reliably determined. This problem can typically be addressed by using a thinner slice thickness where this is possible.

History

It is the nature of the maze of the bronchial tree that a branch which extends locally towards a target location does not actually lead to the target. As a result, a practitioner may frequently find that he has steered into a branch which looked promising but then leads away from the target. In such circumstances, it is valuable to provide a navigation aid to avoid repetition of the error, and to help identify the correct path. For this purpose, the system of the present invention and the corresponding method preferably provide a "record" function which allows selective display of a historical path traveled by the catheter tip.

Specifically, referring to FIGS. 18A-18C, there is shown a path represented by a solid line 152 in all three views. Path 152 represents a path previously followed by the practitioner in trying to reach target 148. Although starting in what appeared the right direction to reach the target, the practitioner found that the path lead to a position posterior to the desired target. At that point, the practitioner actuated the recording mode and withdrew the catheter, thereby generating a line 152 indicative of the path already followed. The practitioner then starts to advance the catheter again slowly, feeling (via the steering mechanism) for an upward branch until he finds the correct route indicated by dashed line 154 which branches off upwards from path 152.

Cyclic Motion Correction

Although the catheter position is measured via location sensor 44 in real time, the target location is not. The target is generally considered fixed relative to the patient's body position which is monitored in real time by sensors 20 (FIG. 1). However, navigation accuracy may decrease as a result of cyclic chest movement resulting from breathing. Preferably, precautions are taken to reduce the effects of this cyclic movement. This may be done by one of a number of techniques, as follows.

According to a first preferred option, position sensor measurements are sampled selectively so that measurements are only made at an extreme of a cyclic motion. The extremes can readily be identified by the cyclic displacement of sensors 20 during the breathing cycle. It may be preferred to use the maximum exhalation state for measurements since this state typically remains steady for a relatively larger proportion of the breath cycle than the maximum inhalation state.

Alternatively, measurements can be taken continuously, and the cyclic variations eliminated or reduced by additional processing. This processing may include applying a low-frequency filter to the measurements. Alternatively, an average of the measurements over a time period of the cyclic motion may be calculated.

Local Distortion Correction

Various techniques were discussed above for achieving registration (translation and/or rotation) of CT data with the reference coordinate system of the measurement system so as to make the CT data available for importing target information and providing real time CT or virtual bronchoscopy displays. In many cases, however, a translation and rotation mapping is not fully satisfactory, especially in regions far from the reference points used to perform registration.

The primary cause of the mismatch between the two coordinate frames is believed to be body posture distortion resulting from the different body postures used for the two procedures. Specifically, in order to maintain constant position during CT scanning, the patient is typically required to hold his breath for the duration of scanning (either in one pass, or subdivided into a number of periods). Furthermore, the patient is required to lift his arms above his head to avoid artifacts which would be caused by the arms within the scanning region. In contrast, a bronchoscopy procedure is performed over an extended period and typically under partial sedation, making it infeasible to request either holding of the breath or raising of the arms for the entire procedure.

Figure 20A:
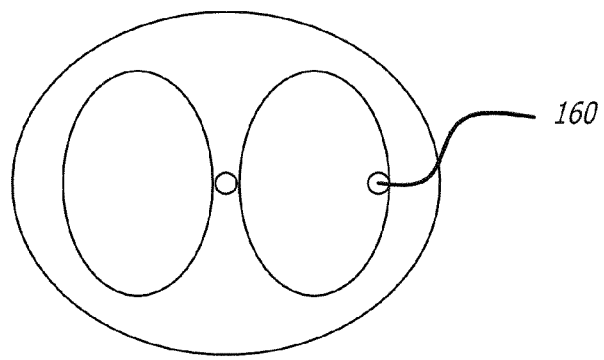
FIGS. 20A-20D are schematic representations explaining a local distortion correction technique for correcting for body posture induced distortion between the CT data and measured positions.
Figure 20B:
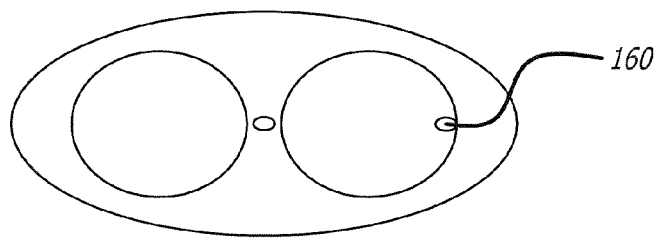
Figure 20C:
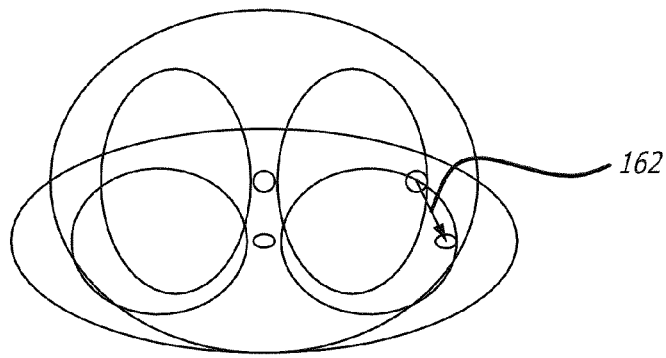
Figure 20D:
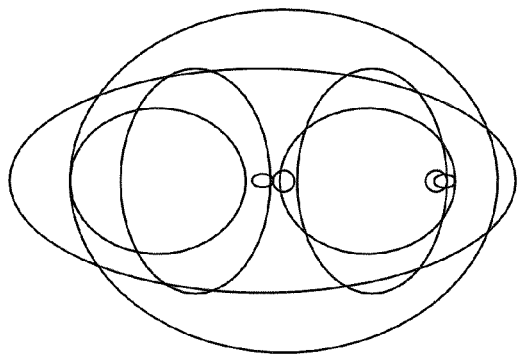

A particularly simple but practical approach to addressing this problem is illustrated schematically in FIGS. 20A-20D. It is assumed that, by requesting that the patient temporarily breath in and raise his arms, it is possible to closely reproduce the body posture and geometry under which the CT scan was performed. This state is represented schematically in FIG. 20A. The "normal" relaxed state of the patient is represented schematically in FIG. 20B. This allows the practitioner to perform a simple localized correction by measuring the position of the catheter tip 160 in the state of FIG. 20A, measuring it again in the relaxed state of FIG. 20B, and using the difference (arrow 162) as a correction vector by which all the CT data is then shifted (FIG. 20D). This procedure can be repeated quickly and easily as many times as required, each time effectively re-aligning the CT data with the region where the catheter tip is currently positioned.

Figure 21:
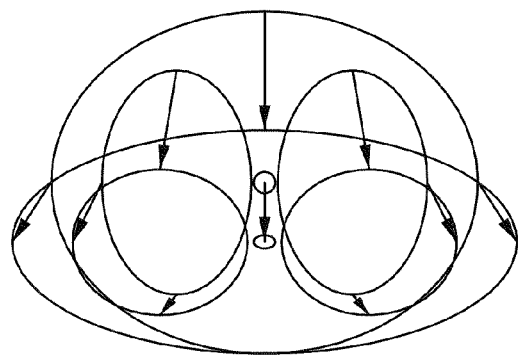
FIG. 21 is a schematic illustration of an alternative implementation of the distortion correction technique by use of a transformation operator.

FIG. 21 illustrates an alternative approach to this issue in which a more comprehensive distorting transformation is used to map the CT data to the current body posture. The data for deriving the required transformation may in principle be derived from repeated measurements as described with reference to FIGS. 20A-20D. Alternatively, where sufficient data is available from the initial registration procedure (by one of the aforementioned registration techniques, or from an alternative source), the entire registration adjustment can be performed from the outset as a distorting transformation which compensates for the body posture related distortion.

Use of Tools

As mentioned earlier, once catheter 30 has successfully been navigated to the target location, guide element 32 is preferably removed, leaving sheath 40 in place as a guide channel for bringing a tool to the target location. In order to ensure stability of the sheath and accurate guidance of a tool to the target, the present invention provides a preferred of use as illustrated in FIG. 22.

Figure 22:
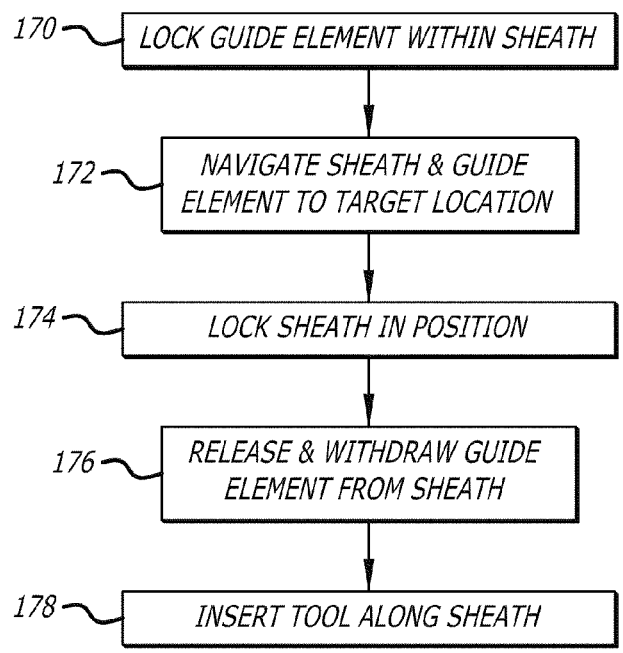
FIG. 22 is a block diagram illustrating a preferred sequence of use of the endoscope according to the teachings of the present invention.

Specifically, FIG. 22 illustrates a preferred method of guiding a medical tool through a branched structure to a target location, where the guide element is first locked within the sheath so as to prevent movement of the guide element relative to the sheath (step 170). The sheath and guide element are then inserted through the working channel of a handle (e.g. part of a bronchoscope) and navigated to the target location (step 172), such as by the techniques described above. The sheath is then locked within the working channel to prevent relative movement of the sheath relative to the handle (step 174). The guide element may then be unlocked and withdrawn from the sheath (step 176). This leaves the lumen of the sheath in place as a guide for insertion of a tool to the target location (step 178).

Sheath 40 may be used as a guide for insertion of substantially any medical tool. Examples include, but are not limited to, biopsy tools such as various kinds of forceps and aspiration needles, and various tools used for ablating malignant tissue that are used in context of a bronchial procedures. Parenthetically, it should be noted that the term "tool" is used herein to refer to the entirety of the elongated structure part of which is inserted along the sheath, and not just the active tip portion. Most standard tools for use via the working channel of a bronchoscope have an external diameter of up to about 1.8 mm, allowing them to fit readily through the lumen of sheath 40.

As an additional safeguard to ensure that the sheath does not get dislodged from the target during withdrawal of the guide element and insertion of a tool, a selectively actuatable anchoring mechanism is preferably associated with a portion of the sheath. The position of the anchoring mechanism along the sheath is generally not critical. Where the target location is in the small diameter airways beyond the reach of a conventional bronchoscope, lateral displacement of the sheath from the target is typically not a problem. It is therefore sufficient to provide anchoring against longitudinal displacement which may be provided in the bronchus or in the nose. Structurally, the anchoring mechanism is preferably implemented as an inflatable element. Alternatively, a mechanically deployed anchoring element may be used. In either case, anchoring mechanisms suitable for this purpose are known in the art.

As a further optional precaution, sheath 40 is preferably provided with a radio-opaque marker to facilitate verification that it has not moved by fluoroscopic imaging. According to a first preferred option, the marker is implemented by treating a distal part of the sheath so as to render it substantially radio-opaque. Alternatively, at least one radio-opaque marker may be attached near or at a distal end of the sheath.

As already mentioned, the present invention can be used with substantially any standard tool. In order to ensure the correct extent of insertion of the tool along sheath 40, it may be preferable to first calibrate the length of the tool. This is preferably performed by inserting the tool before use into a calibration tube which has a length corresponding to a length of the lumen of sheath 40 and marking an extent of insertion on the tool. Marking can be performed simply by applying an "INSERT THIS FAR" sticker to the elongated body of the tool. Alternatively, a clip or the like can be applied to physically obstruct over-insertion of the tool.

Figure 23:
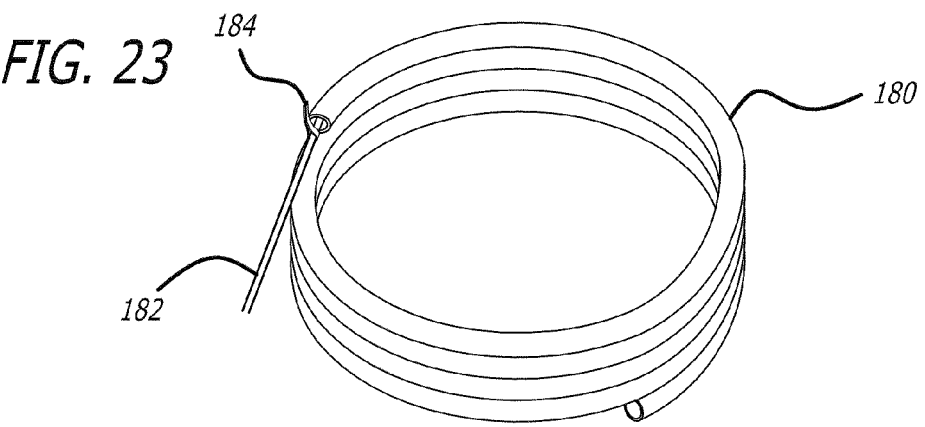
FIG. 23 is a schematic isometric view illustrating the use of a coiled storage tube as a calibration tube for calibrating the length of a tool for use in the endoscope of the present invention.
Figure 24:
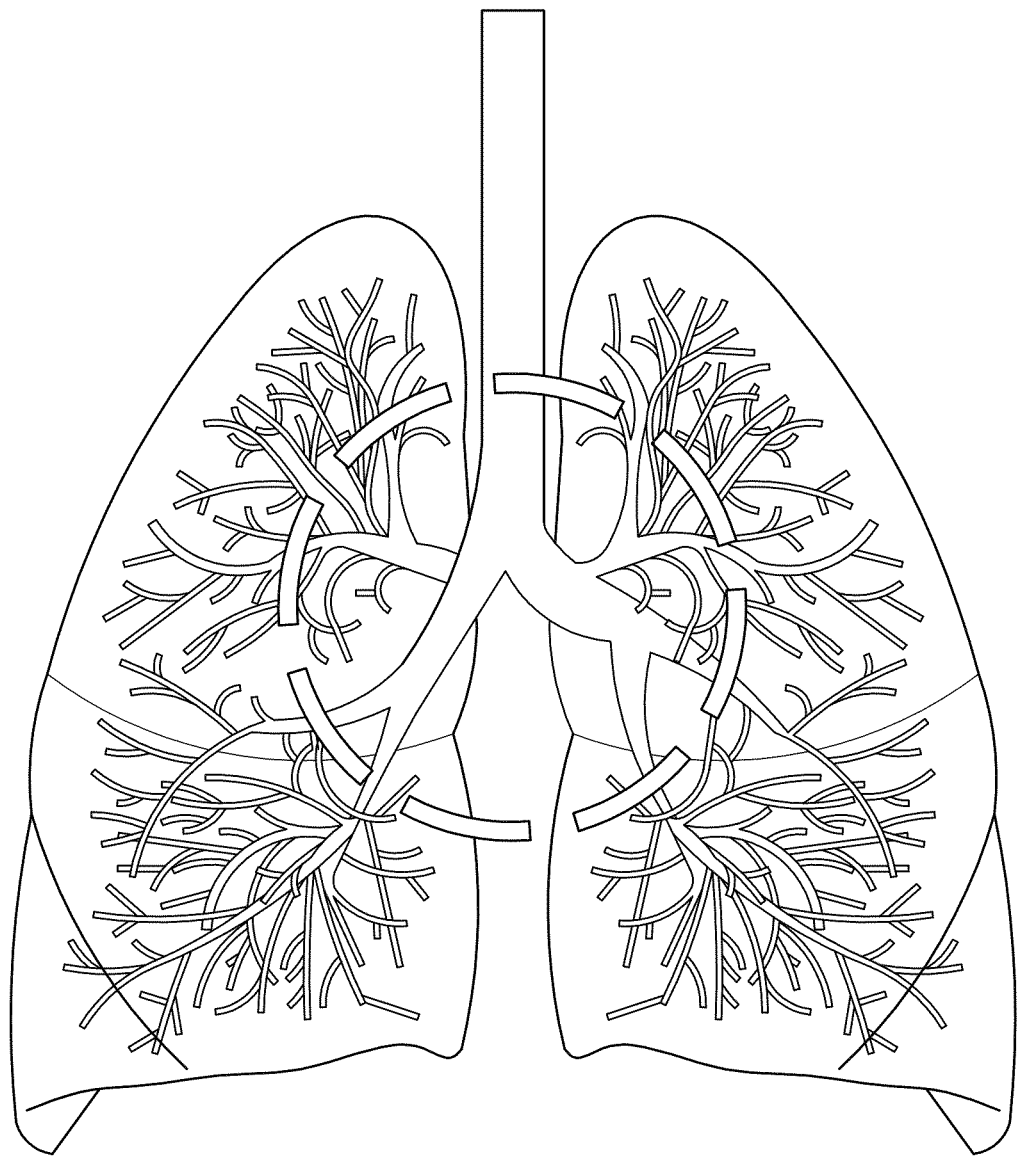
FIG. 24 is a schematic AP representation of the human lungs indicating by a dashed circle the region accessible to a conventional bronchoscope.

In principle, calibration of the tool could be performed using the sheath itself prior to the procedure. It is generally considered preferable, however, to avoid unnecessary wear on the components to be used in the procedure. Instead, as illustrated in FIG. 23, the guide element and sheath are preferably supplied in a coiled storage tube 180 which doubles for use as a calibration tube for calibrating the length of a tool 182. The practitioner then removes the guide element and sheath from storage tube 180 and inserts tool 182 until the end of the tool reaches the end of storage tube 180. The practitioner then marks tool 182 with a sticker or clip 184 as described earlier. Tool 182 is then ready for use.

Miniature Endoscope with Retractable Imaging

As exemplified above with reference to FIG. 7, certain embodiments of the present invention provide a catheter 30 made up of a sheath 40 having a lumen extending from a proximal insertion opening to a distal opening, and a guide element 32 configured for insertion through sheath 40, where the guide element includes at least part of an imaging system 62, and the catheter includes at least one steering mechanism for co-deflecting sheath 40 and guide element 32. It should be noted that this structure, with or without a location sensor, is a highly significant stand alone device with robust functionality.

Specifically, the use of a sheath with a retractable imaging system combines the advantages of a small gauge single lumen catheter with the capabilities of both endoscopic imaging, steerable navigation and tool access. The devices preferably include an optical imaging sensor, such as sensor 62 described above, or part of an optical imaging system such as a light fiber bundle.

A range of variants implementations of such a stand alone device are within the scope of the present invention. Firstly, it should be noted that the steering mechanism may be a conventional unidirectional steering mechanism, and may optionally be included within the sheath rather than the guide element. More preferably, a multi-directional steering mechanism such as that of FIGS. 3-5C is used. Both here and in the above-mentioned embodiments, it should be noted that the steering mechanism may optionally be incorporated within the sheath rather than in the retractable guide element. This provides advantages particularly where the target location is reached by maintaining deflection of the catheter tip, allowing this deflection to be maintained during retraction of the guide and insertion of a tool. A similar result may be achieved by including a second steering mechanism or another mechanical arrangement for "freezing" the state of curvature of the tip of the sleeve, as an addition to the steering mechanism of the retractable guide. This, however, is at the cost of increased sleeve thickness and increased cost.

The device may be combined to advantage with the location measurement system described above, allowing it the full functionality of the system described above without requiring a bronchoscope. All of the options discussed above regarding the image sensor and illumination arrangement are also available here.

As with the aforementioned use of sheath 40, the sheath is preferably provided with a selectively actuatable anchoring mechanism such as those discussed above. Radio-opaque distal marking may also be used to advantage.

Finally, an alternative embodiment of the device includes a retractable radioactivity sensor which can be withdrawn from the sheath with the guide element. Here too, this is of value as a stand-alone device combining the functionality of both a radioactivity sensor and a tool guide in a single lumen device.

It will be appreciated that the above descriptions are intended only to serve as examples, and that many other embodiments are possible within the spirit and the scope of the present invention.

The invention claimed is:

1. A method of guiding a medical tool through a branched structure to a target location, the method comprising:
    (a) inserting a locatable guide surrounded by a sheath through a working channel of a bronchoscope;
    (b) navigating the locatable guide and the sheath to a target location, the locatable guide selectively locked relative to the sheath by a locking mechanism;
    (c) locking the sheath relative to the target location;
    (d) unlocking the locatable guide relative to the sheath;
    (e) removing the locatable guide from the sheath, leaving an open lumen through the sheath; and
    (f) inserting a tool through the lumen to the target location.

2. The method of claim 1, wherein navigating the locatable guide to the target location comprises:
    monitoring data received from a position sensor element disposed in the locatable guide.

3. The method of claim 2 wherein monitoring data received from a position sensor element disposed in the locatable guide comprises monitoring position and orientation data received from said position sensor element.

4. The method of claim 1 wherein locking the sheath relative to the target location comprises locking the sheath relative to a handle through which the sheath is fed during navigation to the target location.

5. The method of claim 1, wherein navigating the locatable guide to the target location comprises viewing an image generated by an image sensor deployed for generating an image in the pointing direction of the catheter.

6. The method of claim 5 wherein navigating the locatable guide to the target location further comprises illuminating a field of view of the image sensor by using at least a distal portion of the sheath as an optical waveguide.

7. The method of claim 6, wherein illuminating a field of view of the image sensor by using at least a distal portion of the sheath as an optical waveguide comprises supplying light to the optical waveguide from at least one light source mounted within the locatable guide.

8. The method of claim 1 wherein inserting a tool through the lumen to the target location comprises: (a) inserting the tool into a calibration tube, the calibration tube having a length corresponding to a length of the lumen; and (b) marking an extent of insertion on the tool.

9. The method of claim 1, wherein locking the sheath relative to the target location includes locking the sheath relative to the bronchoscope.

10. A method of guiding a medical tool through a branched structure to a target location, the method comprising:
  (a) navigating to a target location a locatable guide surrounded by, and temporarily fixed relative to, a sheath;
  (b) fixing the sheath relative to the target location;
  (c) removing the locatable guide from the sheath, thereby leaving an open lumen;
  (d) inserting a tool through the lumen to the target location, wherein inserting the tool through the lumen to the target comprises:
    (a) inserting the tool into a calibration tube, the calibration tube having a length corresponding to a length of the lumen; and
    (b) marking an extent of insertion on the tool.

* * * * *